(12) United States Patent
Bijanki et al.

(10) Patent No.: US 11,241,575 B1
(45) Date of Patent: Feb. 8, 2022

(54) ANXIOLYSIS WITHOUT SEDATION: AWAKE CRANIOTOMY FACILITATED BY CONTINUOUS DIRECT STIMULATION OF CINGULUM BUNDLE

(71) Applicant: Jon Timothy Willie, Atlanta, GA (US)

(72) Inventors: Kelly Cathryn Rowe Bijanki, Decatur, GA (US); Cory Inman, Decatur, GA (US); Nigel Pedersen, Decatur, GA (US); Jon Timothy Willie, Atlanta, GA (US)

(73) Assignees: Kelly C.R. Bijanki, Houston, TX (US); Jon T. Willie, St. Louis, MO (US)

( * ) Notice: Subject to any disclaimer, the term of this patent is extended or adjusted under 35 U.S.C. 154(b) by 28 days.

(21) Appl. No.: 16/121,599

(22) Filed: Sep. 4, 2018

Related U.S. Application Data

(60) Provisional application No. 62/554,551, filed on Sep. 5, 2017.

(51) Int. Cl.
| | | |
|---|---|---|
| *A61N 1/00* | (2006.01) | |
| *A61N 1/05* | (2006.01) | |
| *A61N 1/36* | (2006.01) | |

(52) U.S. Cl.
CPC ....... *A61N 1/0531* (2013.01); *A61N 1/36071* (2013.01); *A61N 1/36096* (2013.01); *A61N 1/36132* (2013.01); *A61N 1/36135* (2013.01)

(58) Field of Classification Search
CPC .............. A61N 1/36096; A61N 1/0531; A61N 1/0534; A61N 1/0536; A61N 1/36071; A61N 1/36092; A61N 1/36082; A61N 1/36132; A61N 1/36135
See application file for complete search history.

(56) References Cited

U.S. PATENT DOCUMENTS

| | | |
|---|---|---|
| 6,128,537 A | 10/2000 | Rise |
| 6,782,292 B2 | 8/2004 | Whitehurst |
| 7,346,395 B2 | 3/2008 | Lozano |

(Continued)

OTHER PUBLICATIONS

Boccard et al. "Deep brain stimulation of the anterior cingulate cortex: targeting the affective component of chronic pain." NeuroReport 2014, 25:83-88. (Year: 2014).*

(Continued)

*Primary Examiner* — Steven O Douglas
(74) *Attorney, Agent, or Firm* — Seyfarth Shaw LLP

(57) ABSTRACT

A method of stimulating a patient's brain comprising delivering an electrical stimulation to at least one electrode causing stimulation of a person's anterior cingulum bundle, or especially causing stimulation of a person's dorsal portion of an anterior cingulum bundle resulting in emotional change(s) in a patient comprising one or more of the following: anxiolysis, mirth, analgesia, improved affective tone, enhanced cognitive focus, increased well-being, engagement, or optimism. Further embodiments contemplate an apparatus. Further embodiments contemplate two implanted electrodes within the dorsal portion of the anterior cingulum bundle spaced between about 5 mm and 8 mm apart, having electrical stimulation parameters of between about 1.0 mA and about 3.5 mA, between about 100 Hz to about 150 Hz, and having a pulse width of between about 100 microseconds to about 200 microseconds.

18 Claims, 21 Drawing Sheets

(56) References Cited

U.S. PATENT DOCUMENTS

| | | | |
|---|---|---|---|
| 7,653,433 B2 | 1/2010 | Lozano | |
| 8,190,264 B2 | 5/2012 | Lozano | |
| 8,467,878 B2 | 6/2013 | Lozano | |
| 9,026,218 B2 | 5/2015 | Lozano | |
| 10,729,354 B2* | 8/2020 | Lee | G06F 19/3481 |
| 10,872,277 B1 | 12/2020 | Wang | |
| 2016/0074663 A1* | 3/2016 | De Ridder | A61N 1/36192 607/59 |

OTHER PUBLICATIONS

Lehto et al. "Orientation Selective Deep Brain Stimulation." Neural Eng. Feb. 2017 ; 14(1): 016016. doi:10.1088/1741-2552/aa5238. (Year: 2017).*

Bote et al."MR imaging reveals signs of temporal lobe epilepsy." Diagnostic Imaging. Aug. 18, 2005. Available online at https://www.diagnosticimaging.com/view/mr-imaging-reveals-signs-temporal-lobe-epilepsy (Year: 2005).*

Parvizi et al. "The Will to Persevere Induced by Electrical Stimulation of the Human Cingulate Gyrus." Neuron. Dec. 18, 2013;80(6):1359-67. doi: 10.1016/j.neuron.2013.10.057. (Year: 2013).*

* cited by examiner

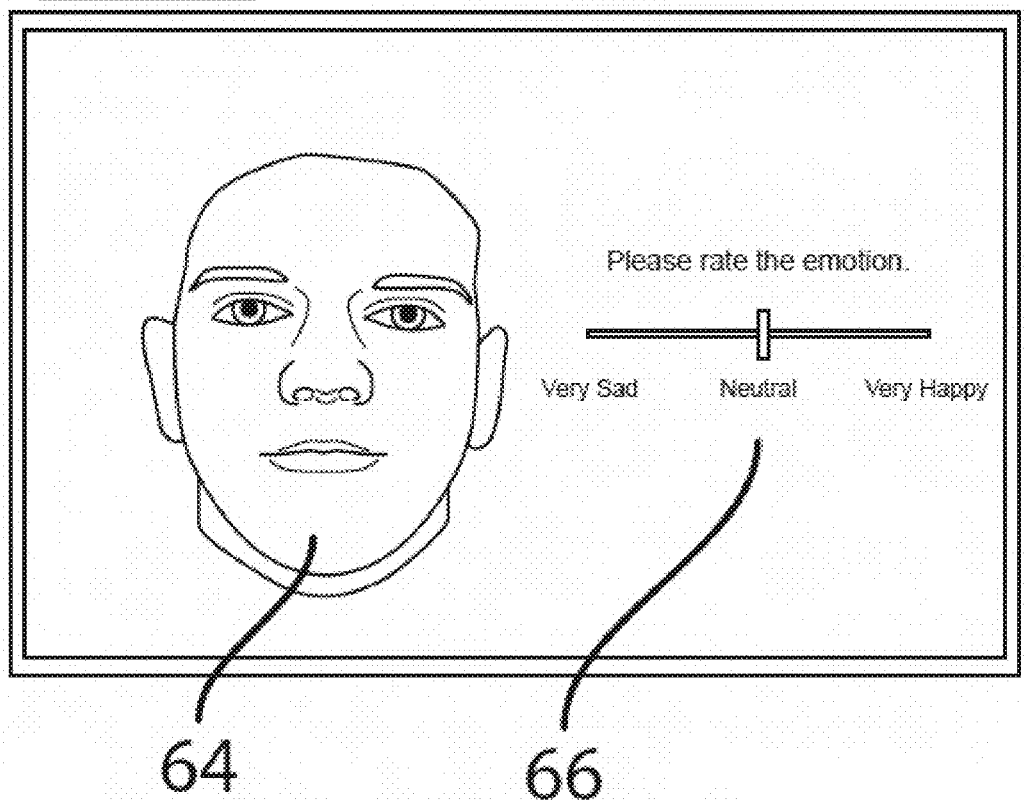

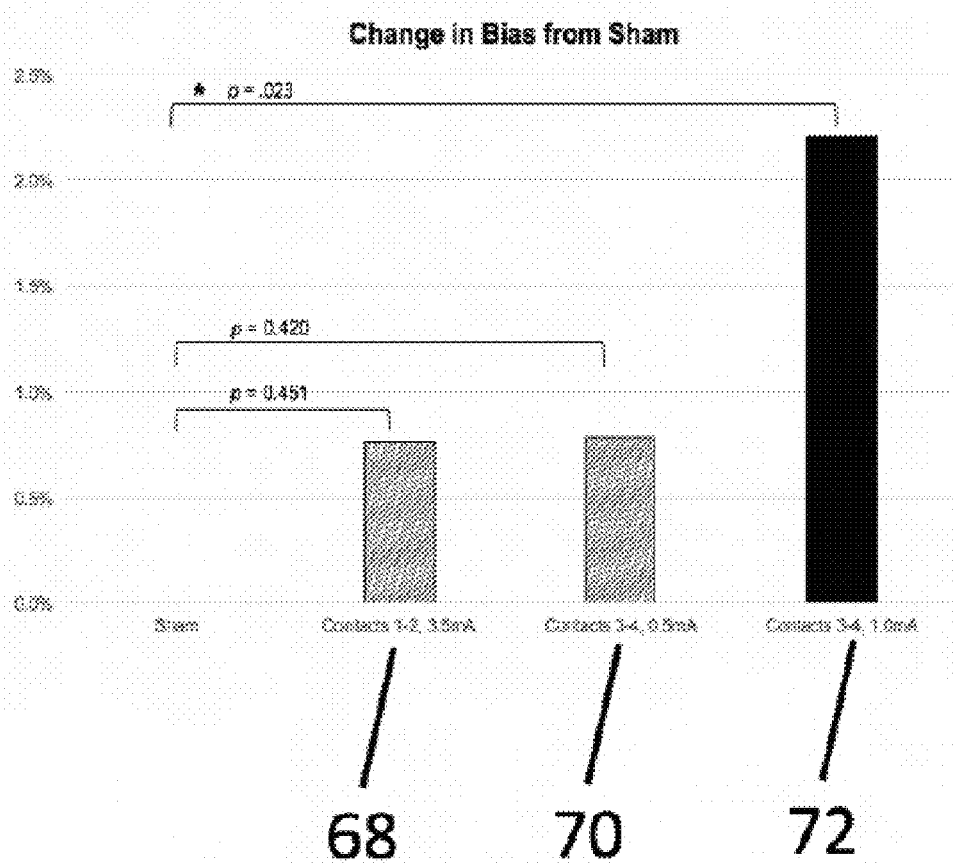

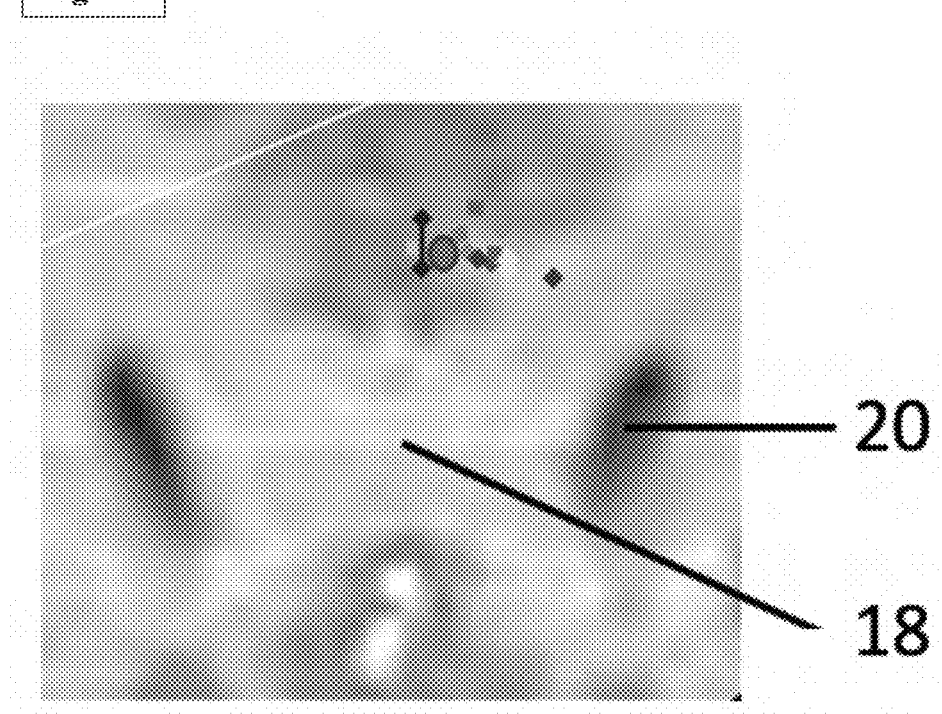

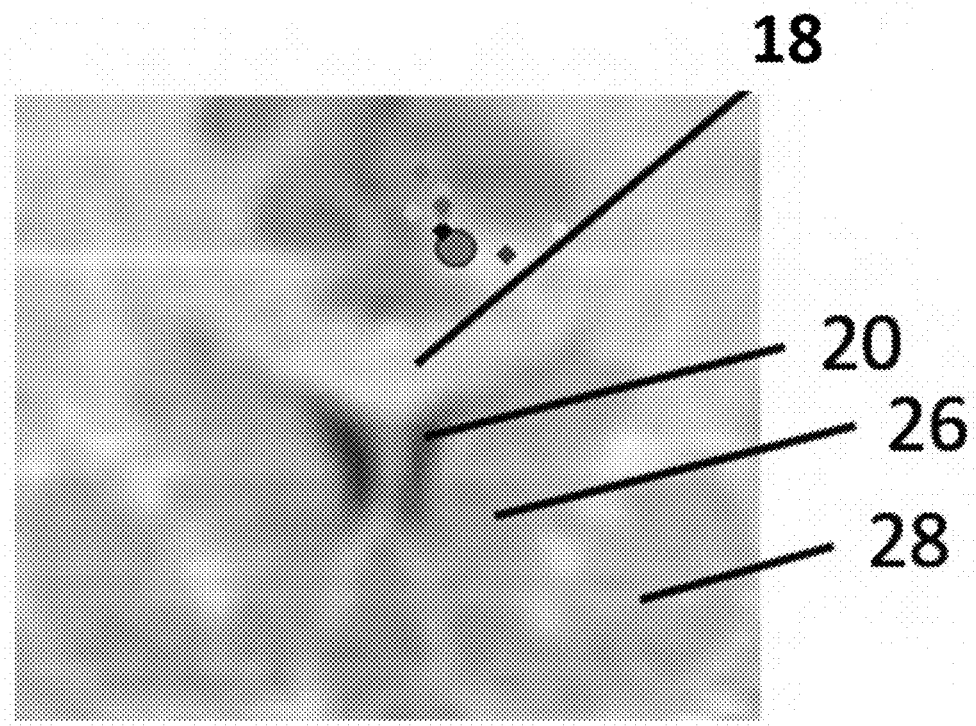

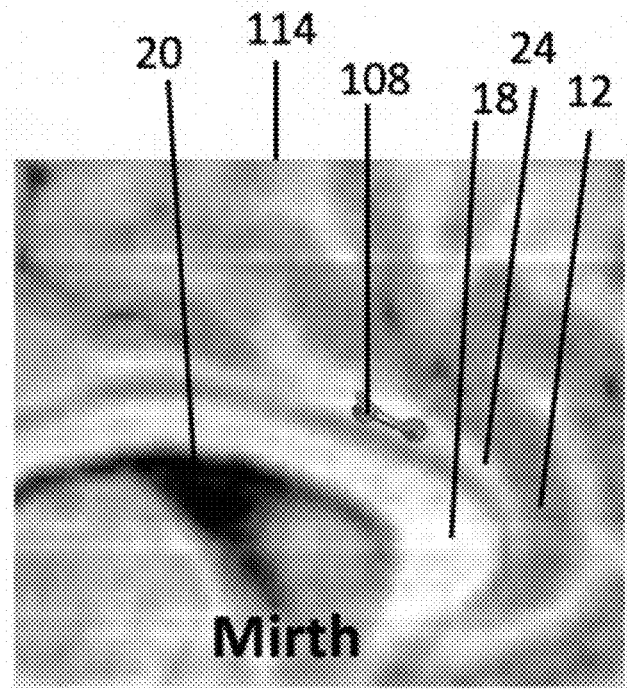

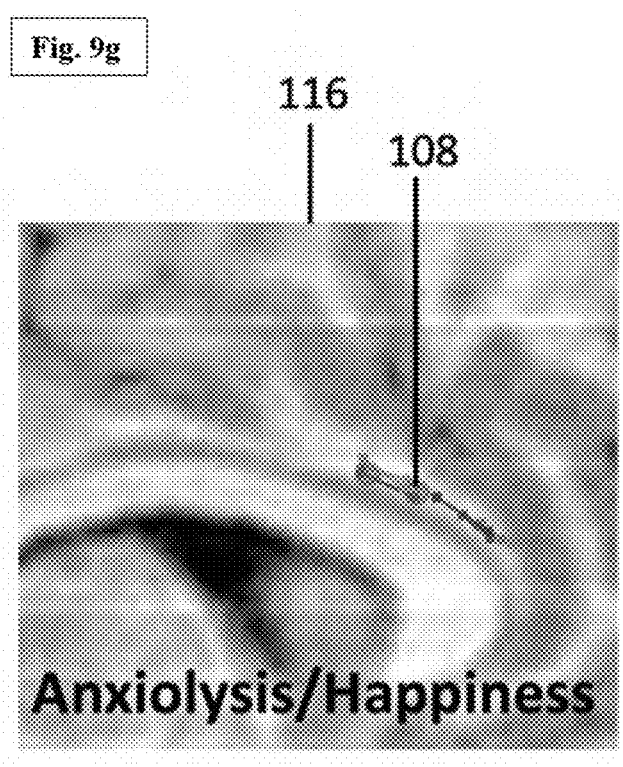

ANXIOLYSIS WITHOUT SEDATION: AWAKE CRANIOTOMY FACILITATED BY CONTINUOUS DIRECT STIMULATION OF CINGULUM BUNDLE

RELATED APPLICATION(S)

This application claims priority to U.S. Pat. Appl. No. 62/554,551 ("Anxiolysis without Sedation: Awake Craniotomy Facilitated by Continuous Direct Stimulation of Cingulum Bundle") which is hereby incorporated by reference in its entirety.

STATEMENT REGARDING FEDERALLY SPONSORED RESEARCH OR DEVELOPMENT

This invention was made with government support by the National Center for Advancing Translational Sciences of the National Institutes of Health under award numbers UL1TR000454 and KL2TR000455. The government has certain rights in the invention.

BACKGROUND OF THE INVENTION

The anterior cingulate has been ascribed putative roles in a wide variety of cognitive and emotional functions, including intention, attention, learning and executive function, reward processing and addiction, emotional salience and empathy, and affective aspects of pain. The anterior cingulate region comprises an allocortical semi-laminar gray matter enveloping the underlying white matter of the cingulum bundle, which runs longitudinally along the extent of the cingulate cortex, wrapping around the corpus callosum from genu to splenium. Previous reports suggest that direct electrical stimulation to the dorsal anterior cingulate cortex, i.e., gray matter, can elicit a transient euphoric and/or analgesic state, though such effects are unusual and inconsistent.

Pharmacological and electrical manipulation of brain function is fundamental to clinical practices of anesthesiology, psychiatry, neurology, and neurosurgery. A problem in anesthesiology is how to independently manage analgesia, anesthesia, sedation, respiratory/autonomic depression, and anxiolysis. Significant baseline anxiety, however, can be an outright contraindication to awake surgery, and emergence of dysphoric agitation during such surgery can lead the clinical team to abort awake mapping if the patient can not be redirected. Typically, doctors prescribe such a patient anxiolytic medications, including but not limited to pain medications, to reduce feelings such as, but not limited to, anxiety. But, these medications also may cause the patient to be unable to accurately provide responses or information to medical care providers. For example, anxiolytic medications, which broadly inhibit neurotransmission, induce sedation or impair executive function, tend to exacerbate dysphoria and are incompatible with the goals of awake surgery. Thus, administration of anxiolytic medications to provide relief for anxiety can be incompatible with the goals of awake surgery.

Many conventional medical procedures prefer or require a patient to be awake. Notwithstanding other such procedures, this issue is present in certain conventional neurosurgeries including but not limited to awake craniotomies that are utilized to definitively identify and protect critical areas of cortex during resections of tumors or for epilepsy. Neurosurgical procedures may be performed in an awake cooperative patient in cases where eloquent cortex (e.g. language processing) must be identified and preserved in the context of resecting infiltrating tumors or lesions associated with epilepsy. Asleep surgery in patients unable to tolerate awake craniotomy risks subtotal resection or unintended neurological deficits. In such an awake procedure, medical care providers prefer that patients provide quick, accurate responses so that the providers can gauge the progress of the surgery decide on next steps during the surgery, but feelings including those of anxiety can interfere with quick and accurate reporting. Providing the patient with anxiolytic medications to attempt to reduce anxiety and achieve the goal of quick, accurate responses can cause the patient to become sedated, further hampering the goal. Thus, for these and other medical procedures where providers prefer or require a patient to be awake, it would be desirable to reduce anxiety without unwanted effects.

BRIEF SUMMARY OF THE INVENTION

Briefly described the invention is summarized as a method of stimulating a patient's brain comprising: placing or identifying at least two electrodes very near to, or in, a portion of an anterior cingulum bundle; delivering an electrical stimulation to the electrodes; wherein such electrical stimulation induces an emotional change in a patient comprising one or more of the following: anxiolysis, mirth, analgesia, improved affective tone, enhanced cognitive focus, increased well-being, engagement, or optimism.

An embodiment of the invention includes a configuration of electrodes where at least one electrode is an anode and at least one electrode is a cathode; and, wherein the electrodes are placed substantially parallel to and within the dorsal portion of the anterior cingulum bundle. Although, embodiments with only a single electrode are contemplated. An embodiment of the invention can be utilized wherein the patient is undergoing an awake surgery, wherein the patient is preparing to undergo an awake surgery, or has recently undergone an awake surgery. Additionally, an embodiment can be utilized wherein the patient has been diagnosed with epilepsy and is undergoing an awake craniotomy related to said diagnosis. Further, an embodiment of the invention can be utilized wherein the patient has been diagnosed with a structural brain abnormality, for example but not limited to a tumor, cavernous malformation, and is undergoing an awake craniotomy related to such diagnosis.

Further embodiments are contemplated wherein an electrical field generated in a patient's brain by said stimulation induces no, or insubstantial, activation of fibers of the corpus callosum. Such embodiments of the invention may have, but are not required to have, at least two electrodes placed in the dorsal portion of the anterior cingulum bundle in a patient's right hemisphere, and at least two electrodes placed in the dorsal portion of the anterior cingulum bundle in a patient's left hemisphere.

Certain embodiments of the invention have electrodes spaced between about 0.5 mm and about 3 inches apart. More preferably, electrodes are spaced between about 5 mm and about 8 mm apart. Typically, but not always, at least one configuration procedure comprising patient self-report, physiological biomarker, and cognitive biomarker is utilized to determine at least one parameter of said electrical stimulation. The at least one parameter of said electrical stimulation would typically comprise one or more of frequency, current or voltage, or pulse width. In certain configurations embodying the invention, said electrical stimulation has parameters comprising over 1.0 mA, between about 50 Hz to about 200 Hz, and having a pulse width of about 90 microseconds to about 450 microseconds. In other configurations embodying the invention, parameters of said electrical stimulation comprise between about 1.0 mA and about 3.5 mA, between about 100 Hz to about 150 Hz, and having a pulse width of about 100 microseconds to about 200 microseconds. In further embodiments of the invention, parameters of said electrical stimulation comprise between about 2.0 mA and about 3.0 mA, about 90 microseconds pulse width; and about 130 Hz.

Certain embodiments of the invention comprise an apparatus configured to stimulate a patient's brain comprising: at least two electrodes in a dorsal portion of an anterior cingulum bundle; at least one power source configured to deliver electrical stimulation to the electrodes wherein said stimulation is configured to induce an emotional change in a patient comprising one or more of the following: anxiolysis, mirth, analgesia, improved affective tone, enhanced cognitive focus, increased well-being, engagement, optimism, or any combination thereof; wherein at least one electrode is an anode and at least one electrode is a cathode. Other embodiments of the invention comprise an apparatus configured to stimulate a patient's brain comprising a means for stimulating a dorsal portion of an anterior cingulum bundle to induce an emotional change in a patient comprising one or more of the following: anxiolysis, mirth, analgesia, improved affective tone, enhanced cognitive focus, increased well-being, engagement, optimism, or any combination thereof.

Other embodiments of the invention include those applied to patients to treat pain or to assist with facilitating the treatment of PTSD. For example, patients who have undergone a surgery related to the patient's spine may have electrical stimulation administered to induce said emotional change comprising at least analgesia; wherein such analgesia is sufficient to reduce administration of some portion of narcotics or some portion of other pharmaceutical drugs that would have otherwise been administered to treat the patient's pain caused by the surgery. Additionally, a certain embodiment may be applied to a patient diagnosed with post-traumatic stress disorder (PTSD), where electrical stimulation is administered to induce an emotional change comprising anxiolysis to facilitate improved cognitive behavioral therapy or improved psychological or psychiatric intervention(s).

BRIEF DESCRIPTION OF DRAWINGS

FIGS. 5a and 5b illustrate an affective bias task stimuli and average ratings across trials in an embodiment.

FIGS. 9a, 9b, 9c, 9d, 9e, 9f, 9g, 9h, and 9i illustrate multiple embodiments of electrode placement in multiple patients, sorted by behavioral phenomena, where the anterior of the brain is on the right of the image.

DETAILED DESCRIPTION OF THE INVENTION

Figure 1A:
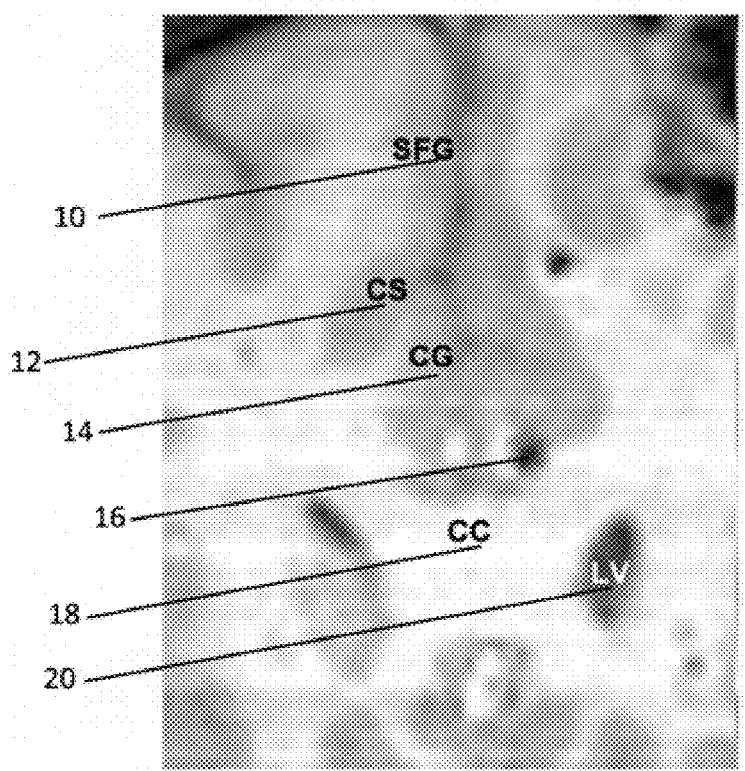
FIGS. 1a and 1b illustrate embodiments of electrode placement in two coronal planes.
Figure 1B:
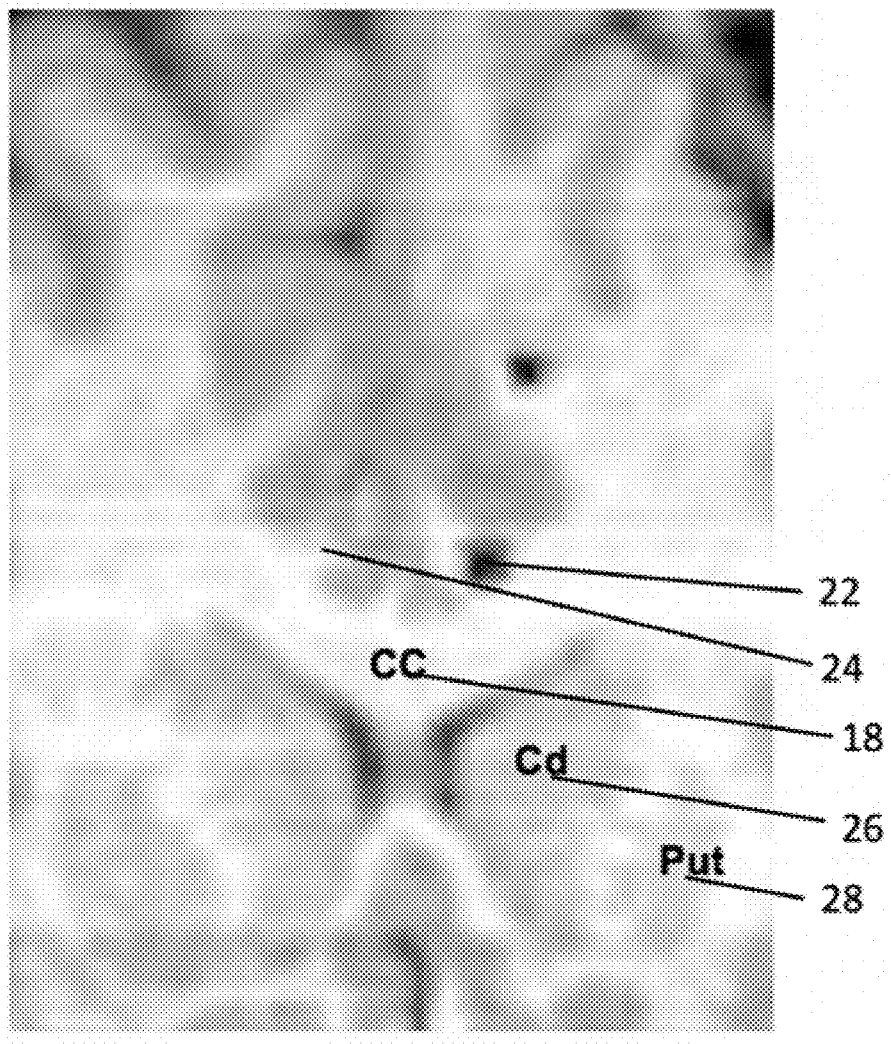

FIGS. 1a and 1b illustrate embodiments of electrode placement in two coronal planes in post-implantation MRI imaging of a single patient. In the embodiment in FIG. 1a, an electrode 16 is shown placed in the cingulum bundle 24, which runs anterior-posterior from front to back of the brain, sitting directly atop the corpus callosum 18. Surrounding brain anatomy is also shown, such as the superior frontal gyrus 10, cingulate sulcus 12, cingulate gyrus 14, corpus callosum transverse-running white matter structure 18, and lateral ventricle 20. FIG. 1b indicates an electrode 22 placed in the cingulum bundle 24.

Figure 2:
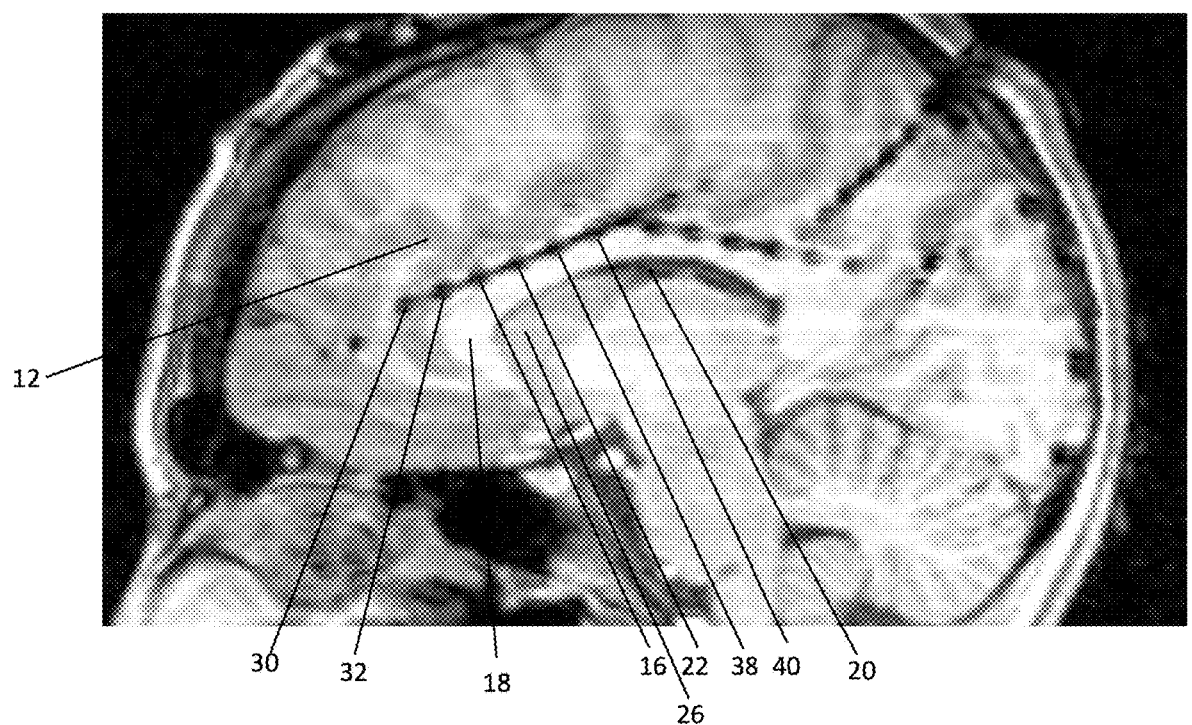
FIG. 2 illustrates an embodiment of electrode placement in the sagittal plane, where the anterior of the brain is on the left of the image.

FIG. 2 illustrates an embodiment of electrode placement in the sagittal plane in post-implantation MRI imaging. In this embodiment, which is a different view of FIGS. 1a and 1b, an embodiment of electrode placement is shown in a single array, e.g., electrodes 16, 22, 30, 32, 38, and 40. The electrodes are part of a stereotactic EEG depth electrode array (Ad-Tech; 0.86 mm diameter, 2 mm length platinum-plated contacts) and are spaced in 8 mm intervals along the cingulum bundle 24. The electrodes 16, 22, 30, 32, 38, and 40 were implanted into the brain parenchyma by the patient's medical providers, in this case a neurosurgeon. In this particular embodiment, due to the length of the array surpassing the dorsal region of the cingulum bundle, electrodes 30 and 32 are placed outside of the cingulum bundle 24 substantially in gray matter and exhibited no effect. Such placement of extra electrodes exhibiting no effect can occur depending on the size of the array compared to the length of the dorsal portion of the cingulum bundle. In this particular embodiment, but not necessarily in other embodiments of the invention, the implantation was for the sole purposes of clinical seizure investigation. When implanted, the impedance of the electrodes 16, 22, 30, 32, 38, and 40 was between 0.3 to 1 kΩ.

Figure 3:
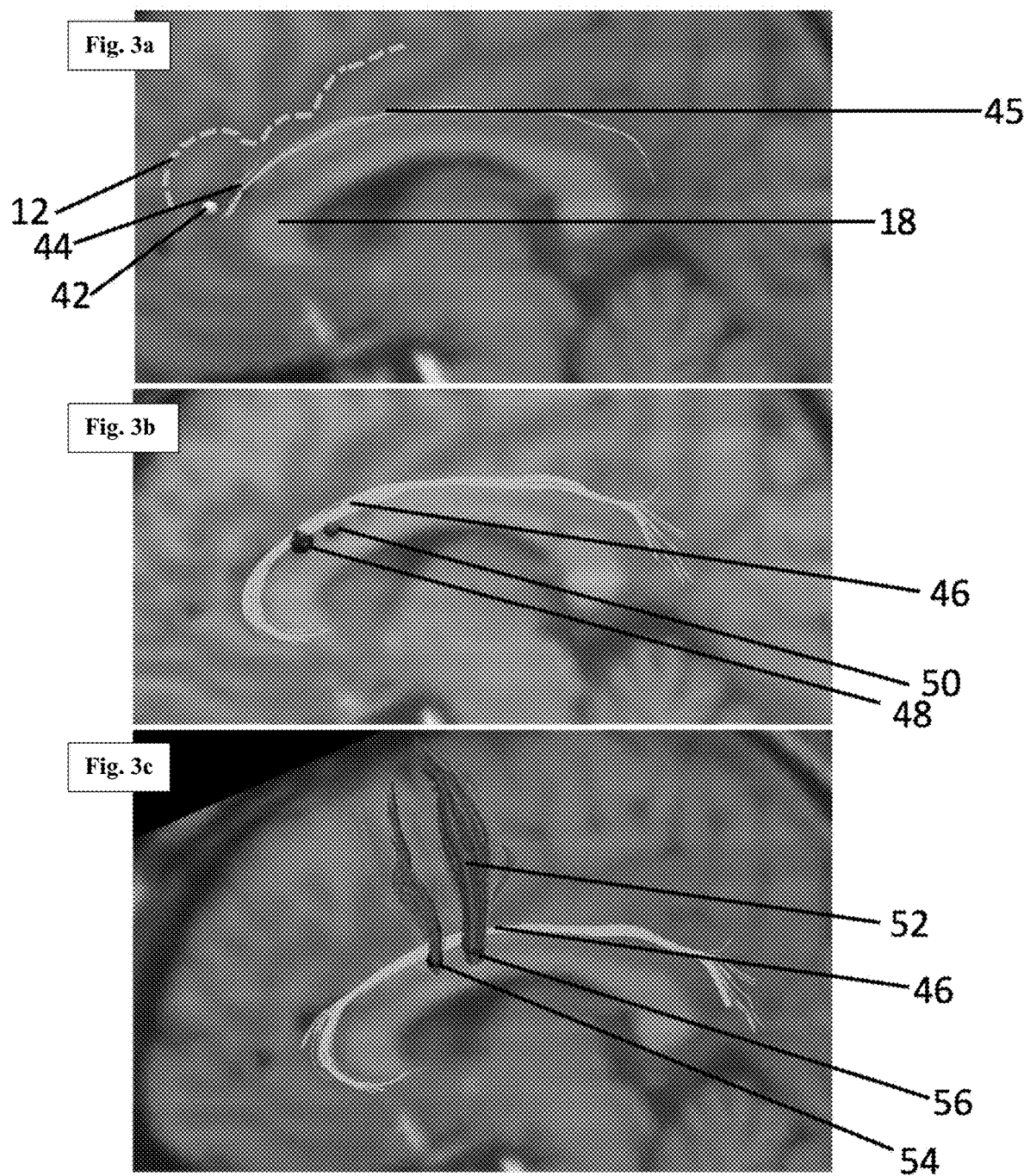
FIGS. 3a, 3b, and 3c illustrate companion sagittal views of probabilistic tractography of stimulated electrodes in an embodiment, where the anterior of the brain is on the left of the image.

In a typical embodiment of the invention, electrodes (including the embodiment shown in electrodes 16, 22, 38, and 40), are placed in the dorsal portion of the cingulum bundle 24. Electrodes should not be placed entirely within the gray matter to achieve advantageous emotional change (s) and/or behavioral effect(s). In further embodiments, the stimulation could be achieved by placing electrodes, including at least one anode and at least one cathode, in a portion of the cingulum bundle 24 near but not strictly within the dorsal portion. In a typical embodiment, electrodes (including the electrodes 16, 22, 38, and 40) are placed substantially linearly to each other on an array running substantially parallel to the cingulum bundle 24 (or running longitudinally within the cingulum bundle 24). Some amount of variation in the substantially linear and substantially parallel placement is expected in embodiments due to the natural curvature, and variation in individuals, of the cingulum bundle 24. However, electrodes intended for stimulation should not be placed substantially orthogonal to the cingulum bundle 24 (or to the dorsal portion of the cingulum bundle 24) because no advantageous effect as identified herein will occur. Additionally, electrodes should not be placed in or near the corpus callosum 18 because unpleasant motor activation may occur. Stimulation of such electrodes generates electrical fields recruiting corpus callosum 18 fibers, which directly innervate primary motor and sensory cortices. (See further discussion of FIG. 3 below and the effects of stimulation of electrodes 38, 40 in Tables 1 and 2). Certain embodiments may have electrodes on separate arrays, where at least one anode and at least one cathode are on different arrays from each other and with different power supplies or power sources. Embodiments are also contemplated where the power supplies or power sources such as non-rechargeable or rechargeable batteries are surgically implanted in an individual for long-term use. In preferred embodiments, typically the at least one anode electrode and at least one cathode electrode are spaced between about 0.5 mm to about 3 inches. In the more preferred embodiments, at least one anode electrode and at least one cathode electrode are spaced anywhere between about 5 mm to about 8 mm. There may be intervening electrodes in between the operative electrodes.

In typical embodiments, stimulation of implanted electrodes is delivered in current-regulated, charge-balanced, biphasic symmetrical rectangular pulses using a human neurostimulator (Cerestim R96, Blackrock Microsystems, Salt Lake City, Utah). In a typical embodiment, stimulation of such parallel placed electrodes in the dorsal portion of the cingulum bundle 24 is titrated (e.g., configured) per patient response from a starting configuration stimulating at 130 Hz frequency, 90 microsecond pulse width, and increasing stepwise levels of current as tolerated by the patient and in the absence of after-discharges or abnormal electrophysiological patterns. Other preferred embodiments may be configured at different frequencies (including but not limited to between about 50 Hz to about 200 Hz), amplitudes (including by not limited to between about 1 mA to about 4.5-5 mA), pulse widths (including but not limited to about 90 microseconds to about 450 microseconds, and most preferred between about 90 microseconds to about 300 microseconds). Additionally, embodiments may configure an anode and cathode by inter-electrode spacing or other manipulable elements. Methods of titration (e.g., configuration) may rely on patient self-report, physiological biomarker read-out (electrophysiology, autonomic nervous system activity), cognitive biomarker read-out (affective bias task or facial motor analysis), and may include incremental steps through each manipulable element or utilizing computer algorithms to optimize search parameters using random walk or other methods. Certain example stimulation parameter embodiments showing an effect, and without limitation to other embodiments, are set forth below in the tables below, e.g., 130 Hz, 300 μs pulse width; 50 Hz, 200 us pulse width; 130 Hz, 300 us pulse width, 2.0 mA.

Following implantation, and titration of stimulation parameters of at least one anode and at least one cathode electrode as described herein and located in the cingulum bundle 24 (preferably linearly to each other on one or more arrays running parallel to the dorsal portion of the cingulum bundle 24), the patient achieves an advantageous consistent feeling of anxiolysis/happiness and/or mirth. Examples of such embodiments are described herein. Anxiolysis/happiness may be operationally defined lexically from a statement of the patient, and/or as a 30% reduction in anxiety reported on a visual-analog scale ranging from 0-10, and mirth may be operationally defined by observation of involuntary laughter or involuntary smiling (i.e., where involuntary means not expressly requested). Such feelings correspond to a reduction in patient anxiety during an awake surgery and increased patient relaxation during an awake surgery, but without sedation or other effects hampering the speed and accuracy of the patient reporting. As an example, in the embodiment in FIGS. 1a, 1b, and 2, stimulation of the electrodes 16, 22, using the former as an anode, and the latter as a cathode, induced feelings of anxiolysis/happiness and mirth in a patient. This is evident in the corresponding portions of Tables 1 and 2 relating to effective stimulation of electrodes 16, 22. Also in the embodiment in FIGS. 1a, 1b, and 2, stimulation of the electrodes 38, 40 elicited mirth (as defined herein), but also unpleasant motor activation; for this particular stimulation, a recording site for single channel and coherence electrophysiological analyses was electrode 38, and such recording occurred immediately before and immediately after stimulation. This is evident in the corresponding portions of Tables 1 and 2 relating to effective stimulation of electrodes 38, 40.

FIGS. 3a, 3b, and 3c illustrate companion sagittal views of probabilistic tractography of stimulated electrodes in the embodiment of FIGS. 1a, 1b, and 2. FIG. 3a shows the border of the cingulate sulcus 12 in a dotted line. FIGS. 2 and 3a indicate that electrodes 30, 32 were implanted in a gray matter portion of the brain, and also indicated are the corresponding spherical diffusion tensor tractography seeds 42, 44 mapping the electrical field and resulting brain activity upon stimulation. These electrodes 30, 32 and resulting electrical field within the brain are not sufficiently in or close to the cingulate bundle 24 to achieve robust engagement of the cingulum bundle 24 fibers (and so do not achieve an anxiolysis/happiness or mirth effect). The minimal engagement is indicated by the volume of the diffusion tensor imaging (DTI) tractography 45 of the cingulum bundle 24 fibers. FIGS. 2 and 3b show electrodes 16, 22 implanted in the dorsal portion of the cingulum bundle 24 and the corresponding spherical diffusion tensor tractography seeds 48, 50. These electrodes 16, 22 and resulting electrical field within the brain are sufficiently in or close to the cingulum bundle 24 to achieve robust engagement of the cingulum bundle 24 fibers (and so do achieve an anxiolysis/happiness or mirth effect). Such robust engagement is indicated by the volume of the DTI tractography 46 of the cingulum bundle 24 fibers. FIGS. 2 and 3c show electrodes 38, 40 implanted in the dorsal portion of the cingulum bundle and the corresponding spherical diffusion tensor tractography seeds 54, 56. These electrodes 38, 40 and resulting electrical field within the brain are sufficiently in or close to the cingulum bundle 24 to achieve robust engagement of the cingulum bundle 24 fibers (and so do achieve an anxiolysis/happiness or mirth effect). Such robust engagement is indicated by the volume of the DTI tractography 46 of the cingulum bundle 24 fibers.

FIG. 3c also shows that in this embodiment the electrodes 38, 40 were placed in a particular region of the dorsal portion of the cingulum bundle 24 such that the electrical field from the stimulation overlapped with a significant quantity of corpus callosum fibers. Stimulation of the electrodes 38, 40 thereby engaged the corpus callosum fibers innervating primary motor and sensory cortices 52 as shown with DTI (in addition to the engagement of the cingulum bundle fibers 46). Such innervation 52 here caused unwanted muscle responses. Implantation of electrodes with overlap of the dorsal portion of the cingulum bundle 24 and the corpus callosum 18 is a preferred embodiment capable of achieving mirth and anxiolysis/happiness, but a more preferred embodiment avoids implantation in or near any region of such overlap. The factors impacting advantageous position of electrode contacts in the cingulum bundle generally (and to avoid such overlap) include curvature of the cingulum bundle, curvature of the corpus callosum, and angle of entry of the electrode array. Ultimately positioning electrodes most centrally in the cingulum bundle 24, i.e., superior/inferior and medially/laterally extent of the bundle, is ideal. Positioning electrodes too far inferior yields overlap with corpus callosum fibers 18 related to motor activation. Positioning too far superior, yields ineffective overlap with the cingulate cortex. Positioning too far medially causes ineffective overlap with the cingulate cortex. Additionally, positioning too far laterally causes ineffective engagement with other white matter systems which could produce undesirable effects or side effects. Put another way, preferred embodiments would have electrodes very near or in the white matter of the cingulum bundle. The most preferred embodiments would have electrodes in, or well within the white matter of the cingulum bundle, and especially preferred in the white matter of the dorsal portion of the anterior cingulum bundle. Various methods of implanting electrodes in the locations described herein could include conventional methods and entry points known in the art, and also more advanced methods such as curved implantation and magnetic guidance.

Figure 4:
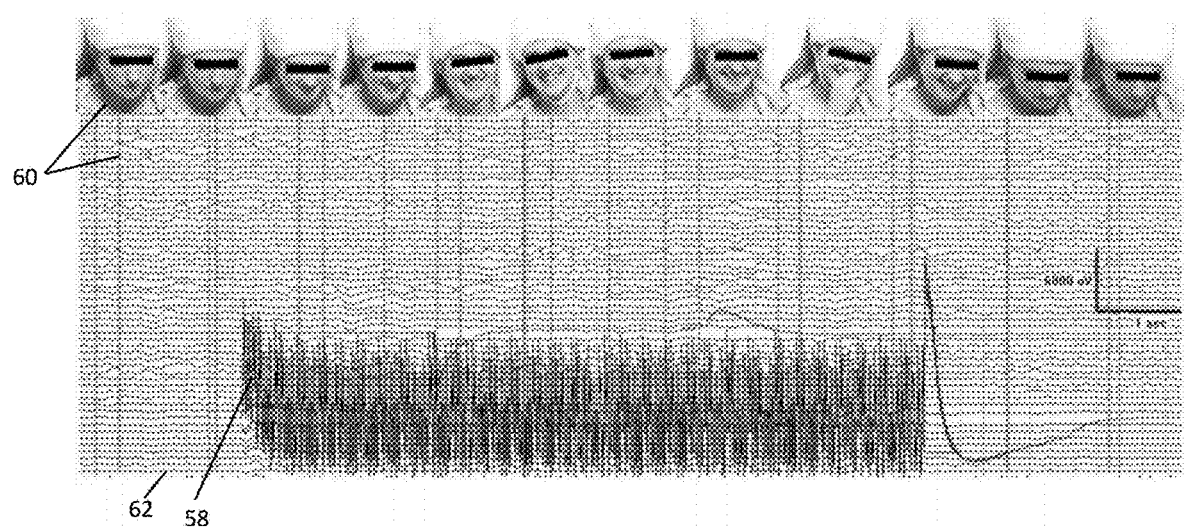
FIG. 4 illustrates temporal evolution of behavioral effects induced by stimulation in an embodiment.

FIG. 4 demonstrates the temporal properties of the behavioral effect observed with stimulation in the dorsal portion of the cingulum bundle in one particular embodiment. In the intracranial EEG recording, the onset of stimulation is evident 58 from high frequency oscillatory activity recorded from the cingulum bundle. In this figure, other waveforms reflect the activity of other parts of the brain during stimulation, showing no abnormality of activity such as epileptiform patterns consistent with seizures. The brain recordings are temporally aligned with video recording, from which a series of time-locked still images are presented 60, demonstrating the evolution of the patient's facial expression prior to, during, and after the offset of stimulation. The patient is observed to tip her head upward, to first smile, then laugh (both involuntary, demonstrating mirth), and then to return to quiescence following the offset of stimulation. In this figure, the time scale is indicated and sub-second time increments are indicated at the level of 200 millisecond demarcations 62. Similar effects to those described in FIG. 4 have been consistently replicated in other patients.

FIG. 5 demonstrates further evidence of emotional change evoked by cingulum bundle stimulation. When presented with an affective bias task (presentation of emotional facial expressions 64 ranging from overt happy to subtle happy to neutral to subtle sad to overt sad with the prompt to rate the emotion of the presented face 66), stimulation evokes a strong positive shift in the perception of emotion in the faces. Specifically, under one embodiment of stimulation of particular electrodes 16, 22 at 1.0 mA, 130 Hz, compared with sham (false) stimulation, the patient exhibits a behavioral response array of 60 emotional faces rated on average 2.25% happier 72. This is consistent with the behavioral observation that the stimulation evoked involuntary smiling and laughter, as well as the patient's self-report that stimulation made her feel happy and relaxed. Stimulation to the same behaviorally active electrodes 16, 22 with a lower current, i.e., 0.5 mA, exhibited a small positive shift in emotional ratings, but no measurable behavioral effect 70. Stimulation to the electrodes 30, 32, which had not been placed sufficiently in or near the cingulum bundle, resulted in no behavioral finding 68. This marker can be utilized during titration, i.e., during optimization of the electrical stimulation parameters to achieve the desired behavioral reponse(s), or emotional change(s) from the patients. Similar effects to those described in FIG. 5 have been consistently replicated in other patients.

Figure 6A:
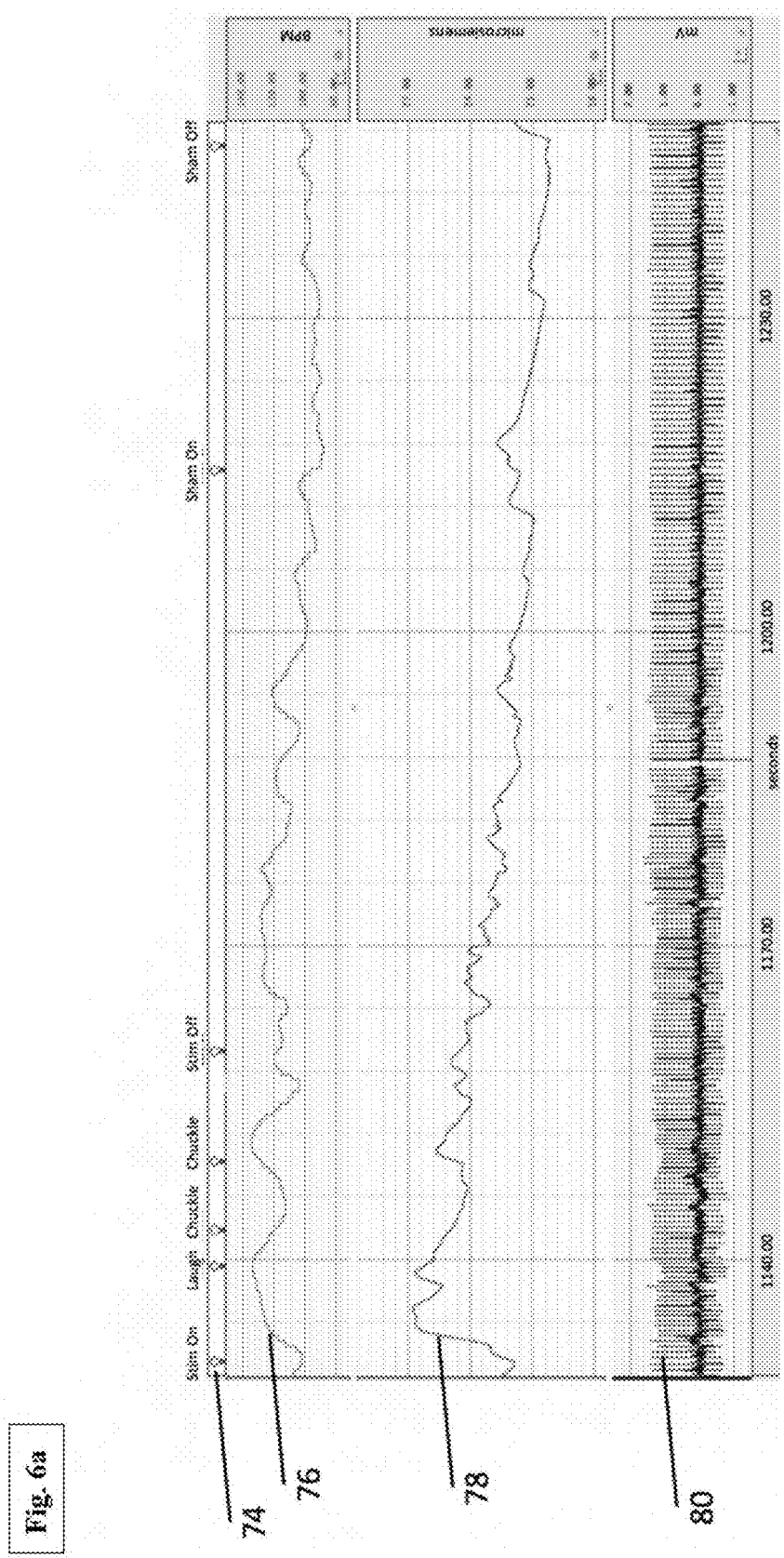
FIGS. 6a, 6b, and 6c illustrate an embodiment of autonomic measures during stimulation to dorsal cingulum bundle increasing current in 0.5 mA steps.
Figure 6B:
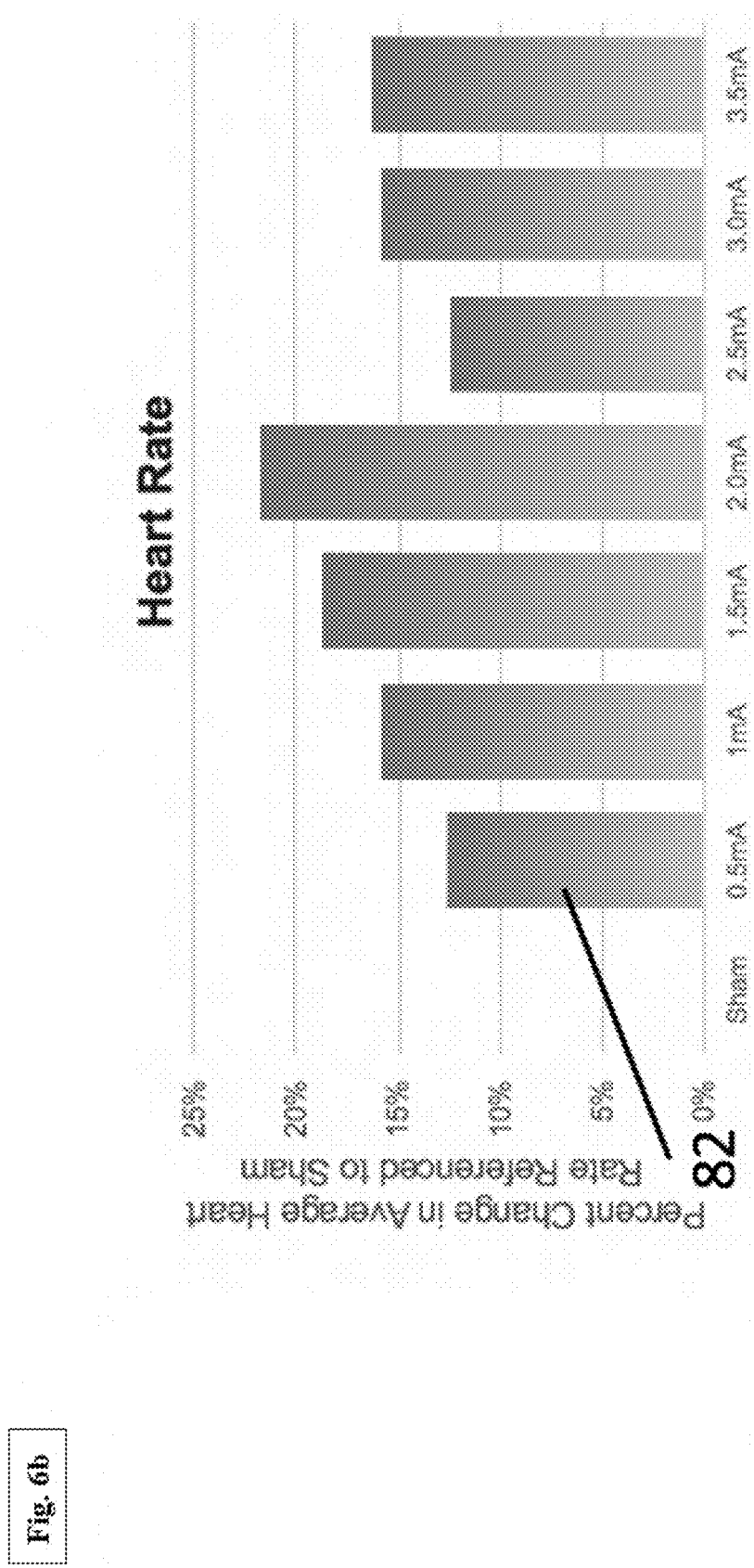
Figure 6C:
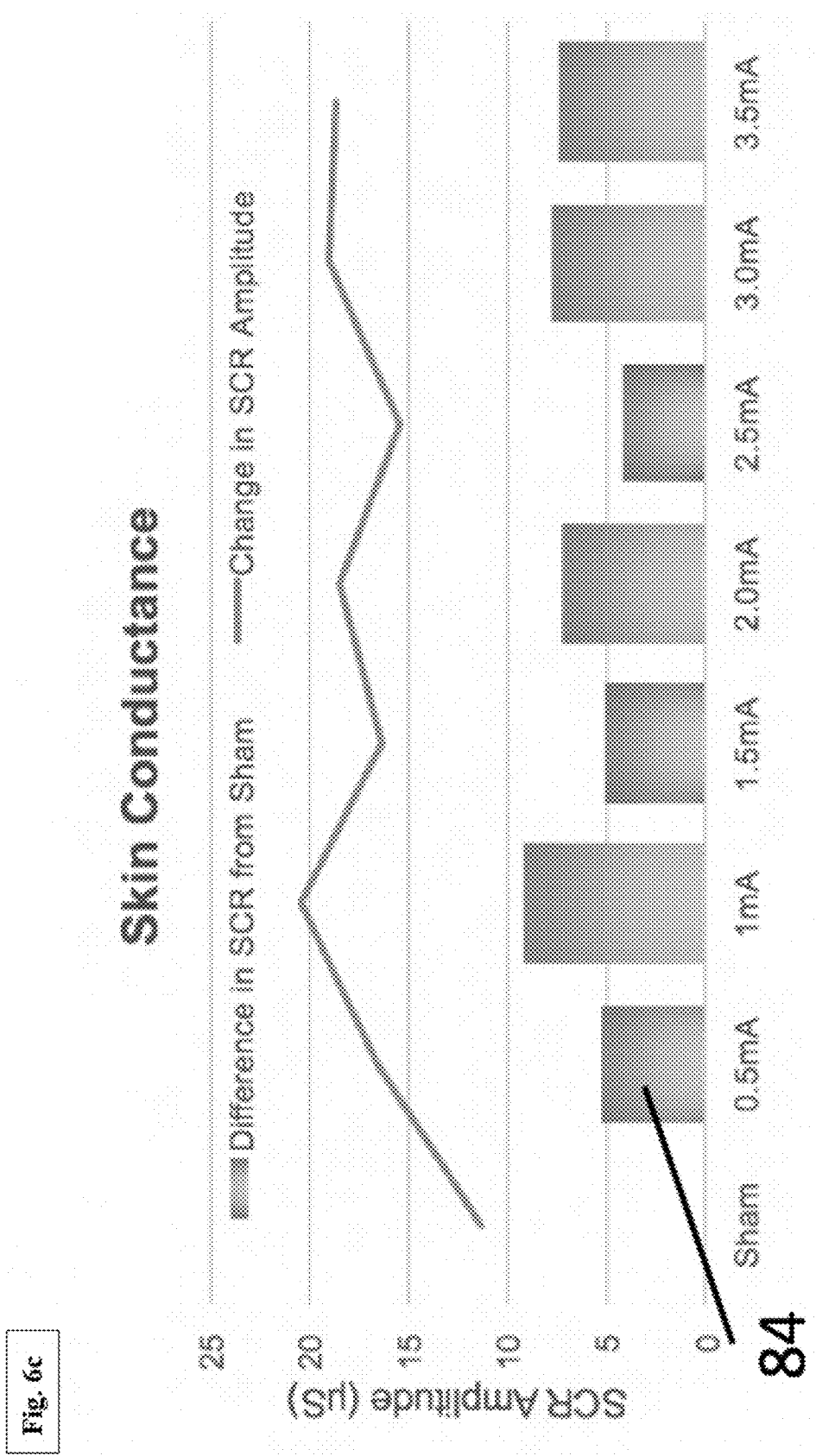

FIG. 6 demonstrates a physiological biomarker of cingulum bundle stimulation one embodiment. The upper panel demonstrates time-locked recordings of patient behavior 74, heart rate 76, skin conductance 78, and raw heartbeat waveforms 80. In this example, onset of stimulation evokes an increase in heart rate and skin conductance. The lower left panel demonstrates a dose-response relationship between heart rate and amplitude of stimulation 82, where greater amplitude, i.e., current, of stimulation typically evokes a stronger change in heart rate. The lower right panel shows no such dose-response relationship for skin conductance—rather, skin conductance is greater with stimulation compared with sham but no incremental relationship is observed. These physiological responses to stimulation may be used as indicators of target engagement during implantation of cingulum bundle arrays, or as biomarkers to track with stimulation status (on or off) during titration and experimental intervention. Stated another way, this marker can be utilized during titration, i.e., during optimization of the electrical stimulation parameters to achieve the desired behavioral reponse(s), or emotional change(s) from the patients. Similar effects to those described in FIG. 6 have been consistently replicated in other patients.

Figure 7A:
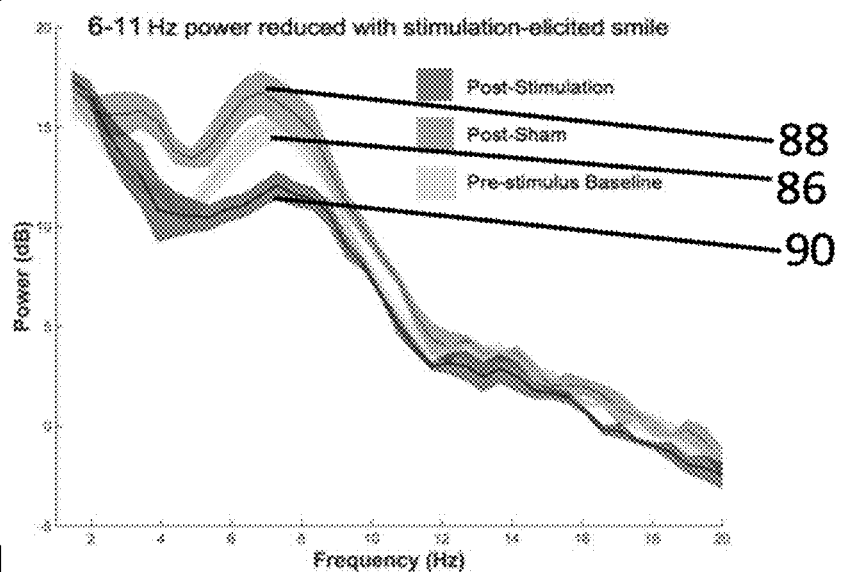
FIGS. 7a and 7b illustrate electrophysiological changes evoked by cingulum bundle stimulation in an embodiment compared with relevant controls.
Figure 7B:
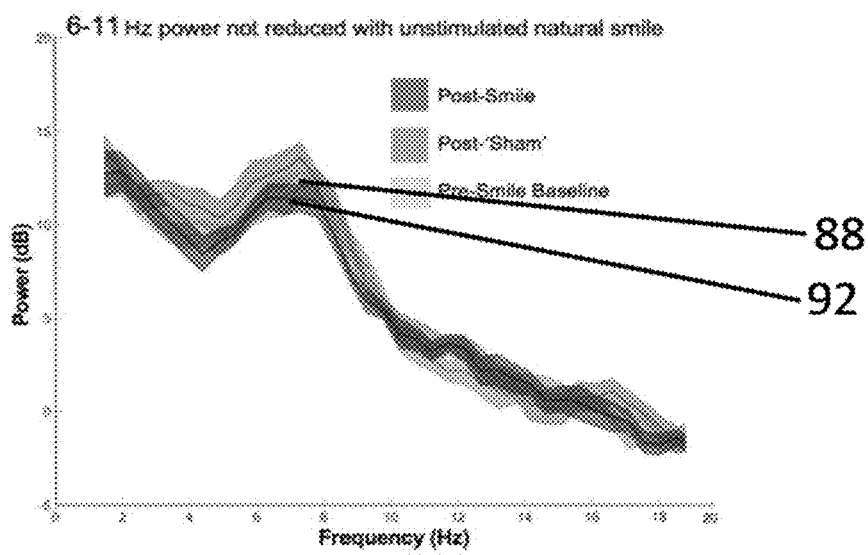

FIG. 7 demonstrates the electrophysiological impacts of an embodiment delivering stimulation to the cingulum bundle. Typically, the cingulum bundle demonstrates an endogenous oscillation (indicating naturally-ongoing neural activity) between 6 and 11 Hz frequency, as recorded from the structure prior to any stimulation 86. FIG. 7 also indicates oscillatory activity following active stimulation 90, compared with following sham stimulation 88, and following an natural smile 92, i.e., socially elicited. Further, FIG. 7 indicates control conditions 88 and 92 to disambiguate effects of stimulation from those evoked by the idea of receiving stimulation 88, or those evoked by the muscular act of smiling 92, since smiling co-occurred with each instance of stimulation in this embodiment. Thus, active stimulation reduces the power of the naturally-occurring oscillation of the cingulum 90. This reduction in power 90 demonstrates an electrophysiological marker or effect unique to active stimulation. This is interpreted to reflect disruption of natural ongoing activity of the cingulum by stimulation. This marker can be utilized during titration, i.e., during optimization of the electrical stimulation parameters to achieve the desired behavioral response(s), or emotional change(s) from the patients. Similar effects to those described in FIG. 7 have been consistently replicated in other patients.

Figure 8:
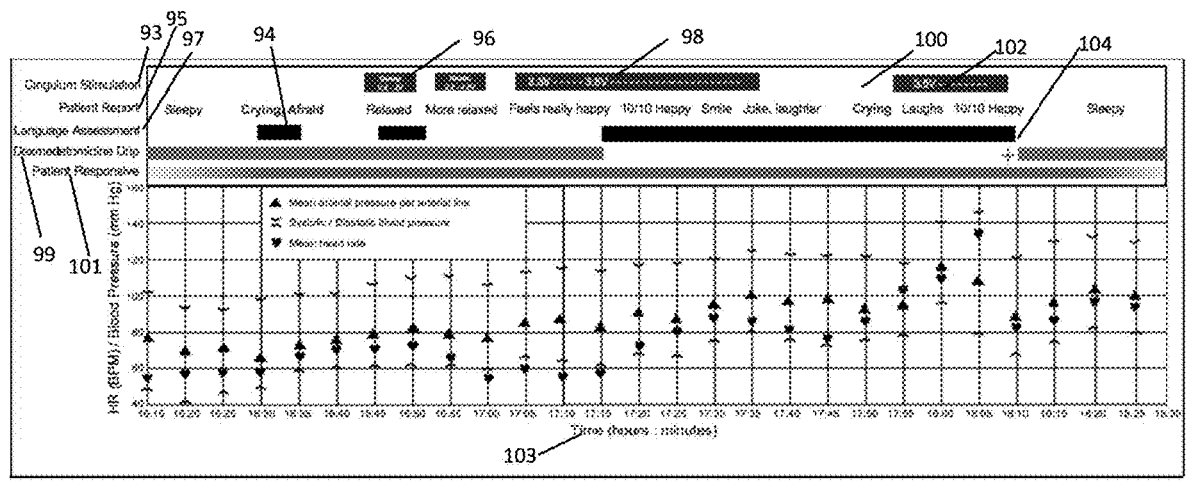
FIG. 8 illustrates the time-course of application of an embodiment to control anxiety during awake brain surgery.

FIG. 8 demonstrates the time course 103 of stimulation in one particular electrical stimulation embodiment applied for the purpose of controlling anxiety in the clinical setting of an awake brain surgery. Heart rate and blood pressure measures are illustrated in FIG. 8 for each five-minute increment of the surgery, and timelines are presented above for applications of cingulum bundle stimulation 93, patient self-reports 95, language assessment activity 97 administration of typical anxiolytic and sedative medication (dexmedetomidine) via intravenous infusion 101, and patient responsiveness or state of consciousness 101. During the following example of a surgery utilizing an embodiment of the invention, without limitation, the medical providers required the patient, who was diagnosed with epilepsy, to be awake and responsive in order to complete language assessment to avoid neurocognitive deficits following the surgery to help treat epilepsy. In FIG. 8, the patient's beginning state during the time course 103 was unconscious under global anesthesia 101. She awakened from anesthesia 101 (as bar becomes dark), became oriented to the surgical environment and reported feeling very afraid 95 at the same time period indicated for the first language assessment 94, 97. The first language assessment 94, 97 was attempted and aborted at this time due to anxiety indicated in the patient report 95 at that same time 103. Stimulation to the cingulum bundle 93 was initiated and titrated (e.g., configured) to the surgical setting 96, during which time the patient reported feeling more relaxed and happy 95. A further language assessment 97 was attempted again but discontinued because the typical anxiolytic, here dexmedetomidine drip 99, appeared to make the patient somnolent and made her speech very slow. The cingulum stimulation 93 provided sufficient anxiolytic benefit and dexmedetomidine 99 was discontinued at the time that titration was completed on cingulum stimulation 98. Language assessment 97 was then successfully completed upon and under such cingulum stimulation 98. Cingulum stimulation 93 was discontinued leading to transient anxiety reported by the patient 100. When cingulum stimulation was re-instantiated 93, 102, the patient immediately resumed reporting feelings of relaxation and happiness and successfully completed the full language assessment task. At the finish of the language assessment, the patient was put back under global anesthesia 104 for the remainder of the surgery, as awake participation was no longer required. This example embodiment of the invention utilized in a clinical application demonstrates the value of embodiments of the cingulum stimulation to 1) control intraoperative anxiety, 2) avoid somnolence and speech disturbances attendant upon typical anxiolytic medications, and 3) to be applied safely with regards to heart rate and blood pressure in the surgical environment. Similar effects to those described in FIG. 8 have been consistently replicated in other patients.

FIGS. 9a through 9i, where the anterior of the brain is on or towards the right of the image, illustrate electrode placements exhibiting certain behavioral responses across a large sample of patients (n=18) using differing configurations, including for placement and stimulation parameters to achieve differing emotional change(s) and/or behavioral effects. As noted, typically titration of electrical stimulation parameters was conducted to achieve desired behavioral effect for each patient, and such routine titration would be typically expected for each embodiment upon placement of the electrodes.

Figure 9A:
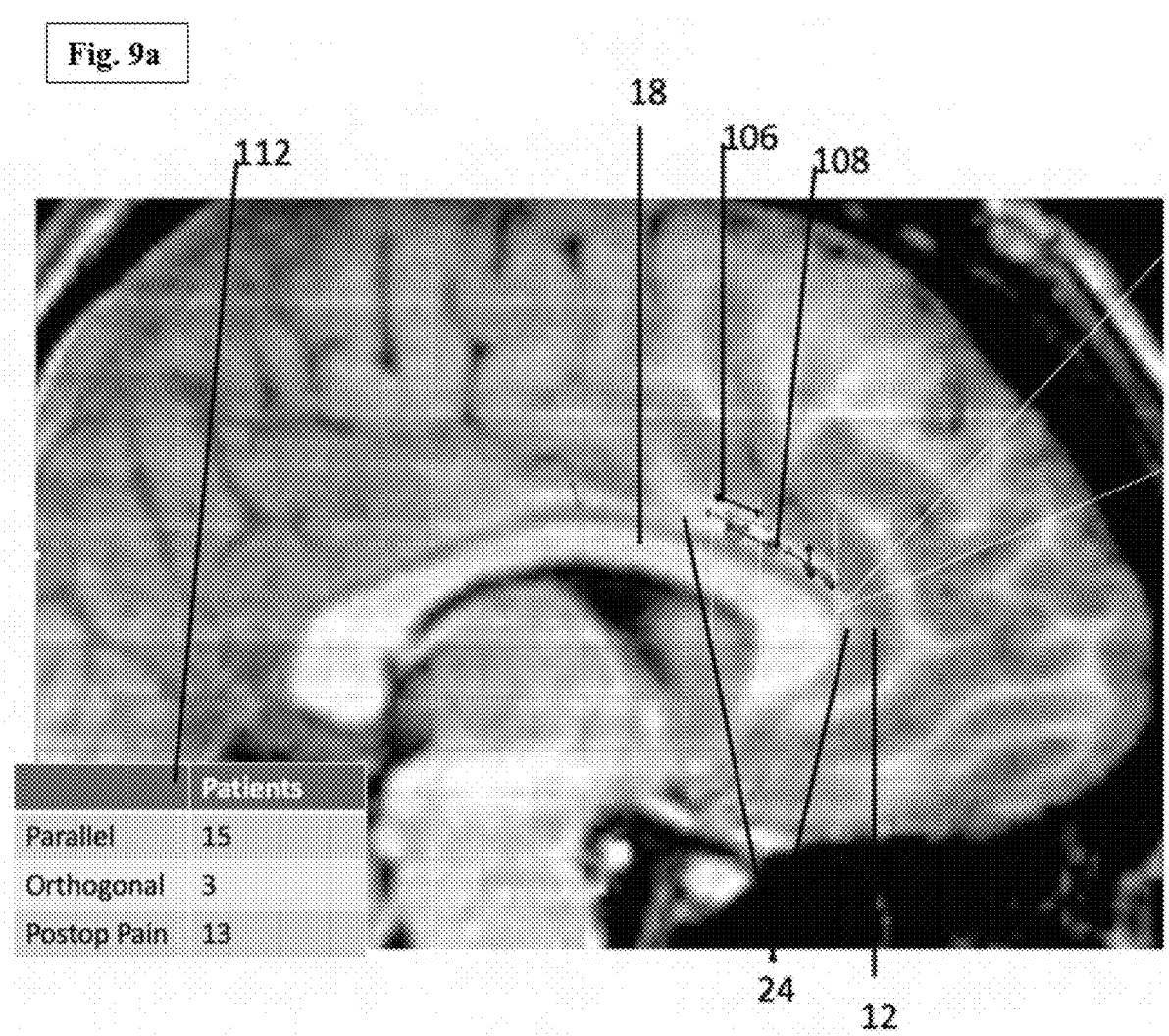
Figure 9B:
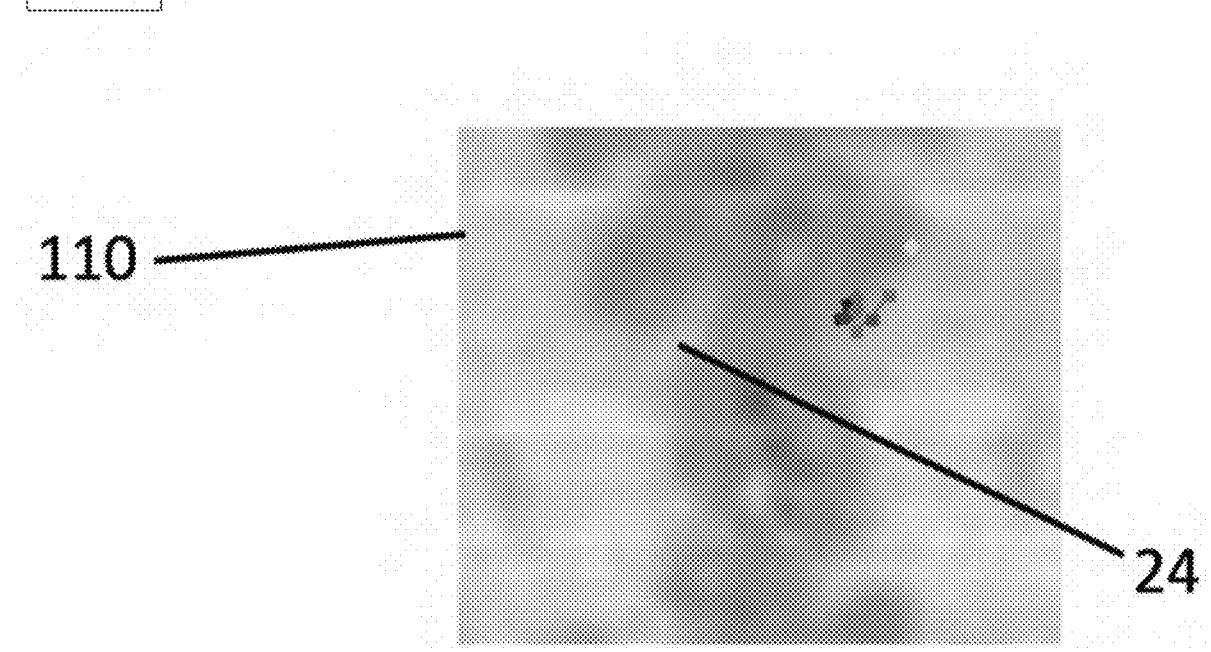

FIG. 9a demonstrates the embodied implanted locations of patients with behavioral responses in or near the cingulum bundle 24. The same patient embodiments in FIGS. 1a, 1b, 2, and 3 are identified are reflected with spherical volumes for anode and cathode 108 (i.e., the index patient). The positions of other patients 106 embodying the implantation electrodes are indicated with diamond shapes for anode and cathode with corresponding connector lines between the electrodes. Fifteen (15) of the patients had stimulated electrodes placed substantially in parallel 112 with the dorsal portion of the cingulum bundle 24. Three (3) of the patients had stimulated electrodes placed substantially orthogonal 112 with the dorsal portion of the cingulum bundle 24. These three patients had no behavioral response. In one of the fifteen patients having a parallel placement embodiment with behavioral effect, a first test of orthogonally placed electrodes yielded no behavioral effect. FIGS. 9b-9d shows a coronal view of the same electrodes identified in FIG. 9a. Each of the electrode placements and resulting electrical fields are sufficiently far from any overlapping regions with the corpus callosum 18 to avoid innervating primary motor and sensory cortices (see FIG. 3c, 52) during stimulation.

Figure 9E:
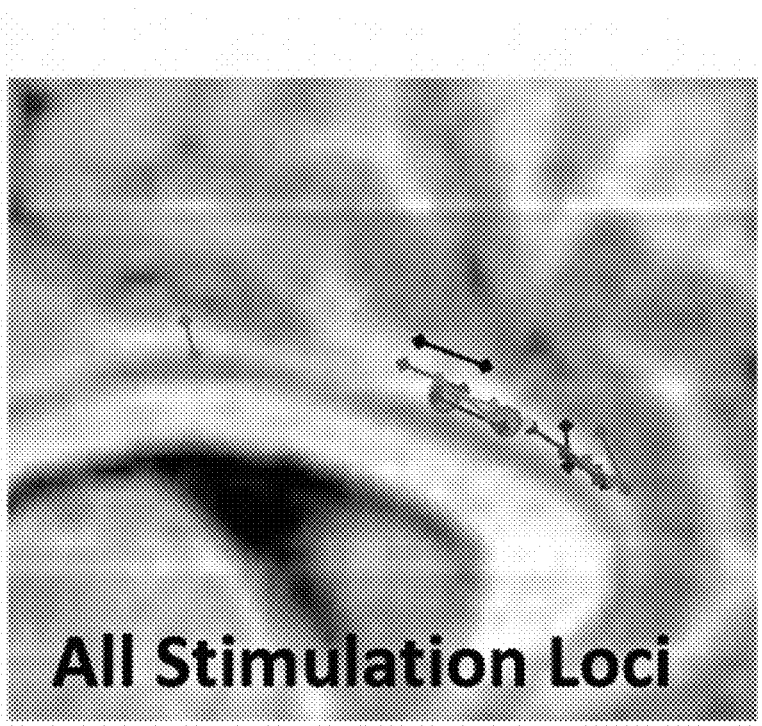
Figure 9H:
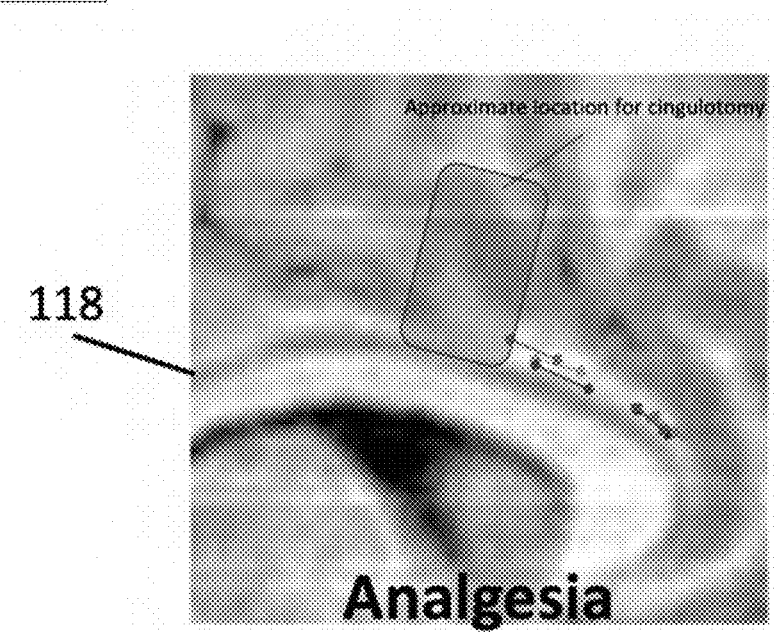
Figure 9I:
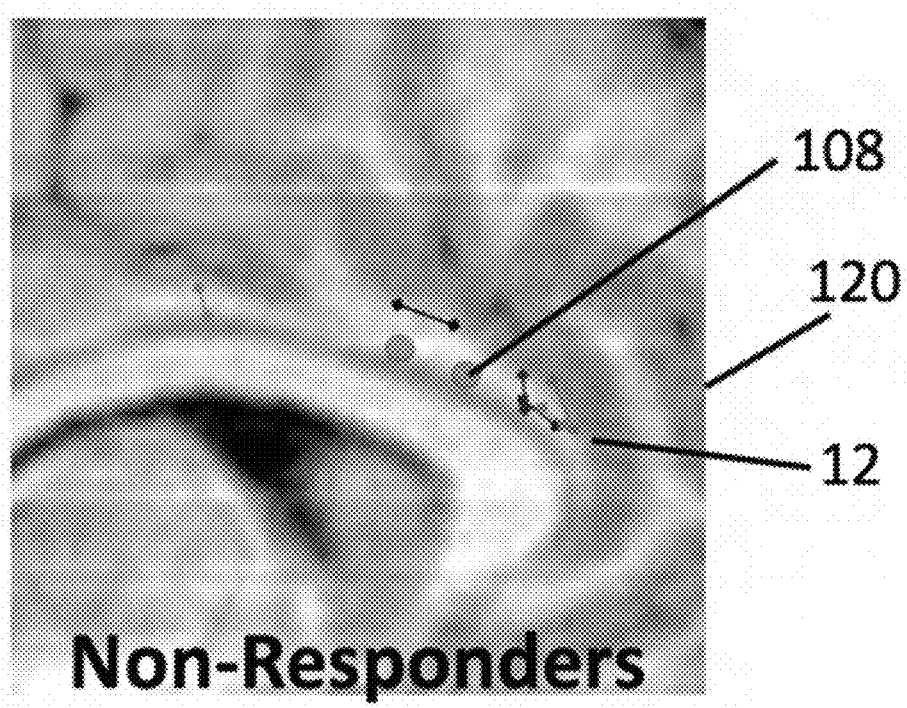

FIGS. 9e-9i indicates behavioral effects of stimulation for various of electrodes, including at least one anode and at least one cathode. FIG. 9e indicates all placements of electrodes. FIG. 9f indicates placement of electrodes 114 where a mirth response (involuntary laughter and smiling) was exhibited. In FIG. 9f the implanted positions of all patients observed to manifest a mirth response 114 had anode and cathode positions very similar to those of the index patient. FIG. 9g indicates placement of electrodes 116 where anxiolysis/happiness was exhibited. These placement locations may be more spread and all anterior in position and oriented parallel to the cingulum bundle as in the index patient. FIG. 9h indicates a surprising exhibit of analgesia measured in certain patients experiencing pain at the time of testing, in this case thirteen of the eighteen patients 112. Those experiencing analgesia 118 showed a similar positional tendency to the anxiolytic responses, again parallel to the cingulum bundle. The box appearing in 9h provides an approximate position for a typical cingulotomy for anatomical orientation. In FIG. 9i, patients showing no behavioral response to stimulation 120 tended to be the most different in position from the index patient, including all implantations orthogonal to the bundle, as well as several positioned too superiorly or anteriorly overlapping the cingulate sulcus 12, or too posteriorly with reference to the positions of the index patient 108 presented in FIG. 9i for positional comparison. Such findings are summarized in chart form in Table 3 below.

With the understanding of the known emotional change(s) and/or behavior effect(s) described in the embodiments herein, certain embodiments of the invention may be applied for the treatment of PTSD. For example, a patient with treatment refractory PTSD could undergo temporary placement of cingulum bundle electrodes, which could be utilized on a temporary basis in a controlled hospital environment to facilitate cognitive behavioral therapy or other psychological or psychiatric intervention. At the conclusion of said intervention, on the basis of bio-behavioral assay, implanted electrodes could be determined to be explanted (removed) or could be made permanent by connecting to a power source implanted in the body.

Further, with the understanding of the known emotional change(s) and/or behavior effect(s) described in the embodiments herein, certain embodiments of the invention may be applied to treat pain occurring in post-operative surgery. For example, prior to or during spine surgery the electrodes described in the embodiments herein could be implanted and the stimulation activated following surgery to reduce pain. Such stimulation could be administered to a patient instead of administering narcotics or other pharmaceutical drugs to treat pain, or as a replacement for some portion of pharmaceutical drugs that would otherwise have been used absent any stimulation. In so doing, a significant risk factor for narcotic dependence or abuse can be reduced or eliminated. Following rehabilitation from surgery, on the basis of bio-behavioral assay, implanted electrodes could be determined to be explanted (removed) or could be made permanent by connecting to a power source implanted in the body.

As demonstrated herein embodiments of the invention, upon titration (for example configuration of the electrical stimulation), achieved the following emotional or behavioral responses or changes: increased or improved cognitive focus, improved affective tone, enhanced cognitive focus, increased well-being, engagement, and/or optimism. All such described responses in embodiments of the invention facilitated the patient's to provide quick and accurate responses during a medical procedure. As an example of one such embodiment, the stimulation allowed for the removal of sedatives commonly used during such procedures (as indicated in FIG. 8 and accompanying text regarding the removal of the dexmedetomidine drip).

While the above discusses embodiments of the invention having at least one anode and at least one cathode it is understood that other embodiments are contemplated where monopolar stimulation in the same region(s), for example and without limitation the dorsal portion of the cingulum bundle 24, can also achieve behavioral responses advantageous for an awake surgery such as without limitation an awake craniotomy.

TABLE 1

Summary of bedside pre-resection observations during sham and active stimulation to left dorsal cingulum bundle of electrodes 16, 22 in FIG. 1.

5 sec stimulation trials (130 Hz, 300 μs pulse width, 10-60 sec inter-stimulation intervals for interview and verbal responses).

| Trials | Current (mA) for 5 sec. | Patient Report and Research Observations |
| --- | --- | --- |
| 1-3 | 0.5 mA | Denies subjective experience. |
| 4-7 | 1.0 mA | Smiles and chuckles involuntarily: reports "feeling something", smiling because she "can't help it". |
| 8-10 | 1.5 mA | Smiles, feels forehead "twitch" (pull upward) and feels smile more on her right, like she is "not in control" as might happen during a seizure, but denies this is her typical semiology. Feels "restless" and a change in mood. "Just a feeling of happiness". |
| 11-12 | 2.0 mA | Smiles and laughs. "It felt the same, just more intense, in a good way . . . That's awesome!". |
| 13 | 2.5 mA | Feels happy, more eyebrow "twitch" (pull upward). |
| 14 | 0 mA (sham) | Denies subjective experience. |
| 15 | 3.0 mA | Smiles and laughs. Feels happy, and a right-sided smile. |
| 16-17 | 3.5 mA | Smiles and laughs. Feeling is more intense, "Wow everyone should have this . . . I'm so happy I want to cry". |

30 sec-stimulation trials with autonomic physiology recording (130 Hz, 300 μs pulse width, 30-60 sec inter-stimulus interval, verbal response, and recovery of autonomic baseline)

| Trial | Current (mA) | EDA | Patient Report and Research Observations |
| --- | --- | --- | --- |
| 1 | 0 mA (sham) | + | Denies subjective experience. |
| 2 | 0.5 mA | + | Denies subjective experience. |
| 3 | 1 mA | ++++ | Smiles and laughs. Feels smiling on the right, happy. Accompanied by large initially positive electrodermal activity (+EDA) response at stimulation onset with slow trend back toward baseline. |
| 4 | 0 mA (sham) | − | No smile or laugh, but reports persistent relaxation and happiness. |
| 5 | 1.5 mA | +++ | Smiles and laughs. Stronger feeling. Could feel it dissipate following the offset of stimulation. |
| 6 | 2 mA | +++ | More persistent laughter. Feels more persistently relaxed. |
| 7 | 0 mA (sham) | − | Denies subjective experience. |
| 8 | 0 mA (sham) | + | Denies subjective experience. No longer feels relaxed, spontaneous thought about pending surgery provokes anxiety. |
| 9 | 2.5 mA | ++++ | "Happy feeling" persisting past the offset of stimulation. |
| 10 | 3.0 mA | ++ | Stronger sensation, lasting longer. Feeling relaxed, denies anxiety. |

TABLE 1-continued

Summary of bedside pre-resection observations during sham and active stimulation to left dorsal cingulum bundle of electrodes 16, 22 in FIG. 1.

| | | | |
| --- | --- | --- | --- |
| 11 | 3.5 mA | +++ | Same feeling as just before, feels involuntary right side smile. |
| 12 | 0 mA (sham) | − | Denies subjective experience; neither relaxed nor anxious, no facial motor feeling. |

Table 1 Legend:
mA = milliampere. EDA = electrodermal activity (skin conductance response). Patient self-report was aggregated by an independent rater who reviewed the videos of all patient testing, transcribed all responses, synthesized summary tables and summary statements. The patient showed a mild (1.5 mS) EDA response with the first sham stimulation, consistent with experimental anticipation. All other sham stimulations elicited EDA responses <1.0 mS, with the exception of trial 8, in which the patient reported a spontaneous thought about pending surgery and reported feeling anxious about it. In the EDA column, − indicates a change of <1.0 mS, + indicates change of 1.0-2.9 mS, ++ indicates change of 3.0-5.9 mS, +++ indicates change of 6.0-9.9 mS, and ++++ indicates change >10.0 mS.

TABLE 2

Trial-by-trial patient self-report during cingulate gray and white matter stimulation and sham.

Left cingulate gray matter stimulation, electrodes 30, 32 (FIG. 1), 50 Hz, 200 us pulse width, 5 sec duration.

| Trial | Current (mA) | Patient Report and Research Observations |
| --- | --- | --- |
| 1 | 0.5 mA | Denies subjective experience |
| 2 | 0.5 mA | Denies subjective experience |
| 3 | 0.5 mA | Denies subjective experience |
| 4 | 1.0 mA | Denies subjective experience |
| 5 | 1.0 mA | Denies subjective experience |
| 6 | 1.0 mA | Denies subjective experience |
| 7 | 1.5 mA | Denies subjective experience |
| 8 | 1.5 mA | Denies subjective experience |
| 9 | 1.5 mA | Denies subjective experience |
| 10 | 2.0 mA | Denies subjective experience |
| 11 | 2.0 mA | Denies subjective experience |
| 12 | 2.0 mA | Denies subjective experience |
| 13 | 2.5 mA | Denies subjective experience |
| 14 | 2.5 mA | Denies subjective experience |
| 15 | 2.5 mA | Denies subjective experience |
| 16 | 3.0 mA | Denies subjective experience |
| 17 | 3.0 mA | Denies subjective experience |
| 18 | 3.0 mA | Denies subjective experience, reports doing okay. |
| 19 | 3.5 mA | Denies subjective experience |
| 20 | 3.5 mA | Denies subjective experience |
| 21 | 3.5 mA | Patient reports no feeling from stimulation, feels "neutrally anxious". |

Left cingulate gray matter stimulation, electrodes 30, 32 (FIG. 1), 130 Hz, 300 us pulse width, 5 sec duration.

| Trial | Current (mA) | Patient Report and Research Observations |
| --- | --- | --- |
| 1 | 0.5 mA | Denies subjective experience |
| 2 | 0.5 mA | Denies subjective experience |
| 3 | 0.5 mA | Denies subjective experience |
| 4 | 1.0 mA | Denies subjective experience |
| 5 | 1.0 mA | Denies subjective experience |
| 6 | 1.0 mA | Denies subjective experience |
| 7 | 1.5 mA | Denies subjective experience |
| 8 | 1.5 mA | Denies subjective experience |
| 9 | 1.5 mA | Denies subjective experience |
| 10 | 2.0 mA | Denies subjective experience |
| 11 | 2.0 mA | Denies subjective experience |
| 12 | 2.0 mA | Denies subjective experience |
| 13 | 2.5 mA | Denies subjective experience |
| 14 | 2.5 mA | Denies subjective experience |
| 15 | 2.5 mA | Denies subjective experience |
| 16 | 3.0 mA | Denies subjective experience |
| 17 | 3.0 mA | Denies subjective experience |
| 18 | 3.0 mA | Denies subjective experience |
| 19 | 3.5 mA | Denies subjective experience |
| 20 | 3.5 mA | Denies subjective experience |
| 21 | 3.5 mA | Denies subjective experience |

TABLE 2-continued

Trial-by-trial patient self-report during cingulate gray and white matter stimulation and sham.

Left cingulum white matter stimulation, electrodes 16, 22 (FIG. 1), 130 Hz, 300 us pulse width, 5 sec duration.

| Trial | Current (mA) | Patient Report and Research Observations |
|---|---|---|
| 1 | 0.5 mA | Denies subjective experience |
| 2 | 0.5 mA | Denies subjective experience |
| 3 | 0.5 mA | Denies subjective experience |
| 4 | 1.0 mA | Denies subjective experience |
| 5 | 1.0 mA | Patient reports that she "kinda feels something", begins smiling involuntarily, reports feeling a little confused. |
| 6 | 1.0 mA | Patient immediately smiles, "I'm smiling because I can't help it", then reports that she felt it for the past 3 stimulations (all three times that 1.0 mA stims were run). |
| 7 | 1.0 mA | Patient smiles and laughs, reports that she feels the same feeling as before (when the 1.0 mA stims were run). |
| 8 | 1.5 mA | Patient smiles, reports feeling her eyebrows twitch and smiling on her right side, "feels kinda like a seizure" and feeling a little confused because something is happening to her that she doesn't understand. |
| 9 | 1.5 mA | Patient smiles, "I feel something", reports that it makes her feel a little restless, feels like there's a change in her mood. |
| 10 | 1.5 mA | Patient smiles, "No memories or anything, just a feeling of happiness", involuntary smile. |
| 11 | 2.0 mA | Patient smiles, "It felt the same, just more intense", in a good way. |
| 12 | 2.0 mA | Patient smiles, "That's awesome!" |
| 13 | 2.5 mA | Patient reports feeling the same (happy), feeling her eyebrows twitch more with this stimulation. |
| 14 | Sham | Denies subjective experience |
| 15 | 3.0 mA | Patient immediately smiles and laughs, reports feeling the same, feeling the smile more on her right side. |
| 16 | 3.5 mA | Patient immediately smiles and laughs, "Wow everyone should have this", more intense than the previous stimulations. |
| 17 | 3.5 mA | Patient immediately smiles and laughs, "I'm so happy that I wanna cry basically". |
| 18 | Sham | Run during affective bias task, patient denies subjective experience |
| 19 | Sham | Run during affective bias task, patient denies subjective experience |
| 20 | 0.5 mA | Run during affective bias task, patient denies subjective experience |
| 21 | 0.5 mA | Run during affective bias task, patient denies subjective experience |
| 22 | 1.0 mA | Run during affective bias task, patient smiles and laughs, reports that she felt relaxed and still felt happy. |
| 23 | 1.0 mA | Run during the affective bias task, patient smiles, reports that the feeling is in no way bothersome. |

Left cingulum white matter stimulation, electrodes 16, 22 (FIG. 1), 50 Hz, 200 us pulse width, 5 sec duration.

| Trial | Current (mA) | Patient Report and Research Observations |
|---|---|---|
| 1 | 0.5 mA | Denies subjective experience. |
| 2 | 0.5 mA | Denies subjective experience. |
| 3 | 1.0 mA | Denies subjective experience |
| 4 | 1.5 mA | "I can really feel that, my mind is at ease", reports feeling more relaxed. |
| 5 | Sham | Reports feeling the same, relaxed. |
| 6 | 2.0 mA | Patient reports feeling a high, relaxed feeling, more intense than previous stimulations. |
| 7 | 2.5 mA | Patient smiles on the right side of mouth, reports that on previous stimulations she could control smiling and laughing, but had less control during this one. |
| 8 | 3.0 mA | Patient reports feeling the sensation more on her right side. |
| 9 | Sham | Denies subjective experience |
| 10 | 3.5 mA | Patient reports that she can feel the same sensation but it is not the most intense one, still feels the sensation on the right side. |

Left posterior cingulum white matter stimulation, electrodes 38, 40 (FIG. 1), 130 Hz, 300 us pulse width, 5 sec duration.

| Trial | Current (mA) | Patient Report and Research Observations |
|---|---|---|
| 1 | 0.5 mA | Denies subjective experience |
| 2 | 0.5 mA | Denies subjective experience |
| 3 | 0.5 mA | Denies subjective experience |
| 4 | 1.0 mA | Denies subjective experience |
| 5 | 1.0 mA | Denies subjective experience |
| 6 | 1.0 mA | Denies subjective experience |
| 7 | 1.5 mA | Patient reports a high sensation, not confused, doesn't feel anything different in face, feels like previous stimulations. |
| 8 | 1.5 mA | Patient reports feeling the same high sensation, not unpleasant, feeling diminishes over time. |
| 9 | 1.5 mA | Patient reports the same feeling, feeling diminishes over time. |
| 10 | 2.0 mA | Patient reports feeling "almost paralyzed", like she was going to have a seizure, felt a little scared and anxious because she felt like she was going to have a seizure, felt back to normal before moving onto next stimulation. No seizure activity noted on intracranial EEG. |
| 11 | 2.0 mA | Patient reports that "it feels like too much", feeling it more on the right side which is typical of her seizures, it scared her a little. |
| 12 | 1.0 mA | Patient reported that she felt the same, just much less intense, more of a happy feeling. |
| 13 | 0.5 mA | Patient reported feeling the same happy feeling, just not as strong. |
| 14 | 0.5 mA | Denies subjective experience |
| 15 | Sham | Denies subjective experience |
| 16 | Sham | Denies subjective experience |
| 17 | 0.5 mA | Denies subjective experience |
| 18 | 1.0 mA | Patients reports a happy feeling but "it's not super strong", very pleasant feeling. |

Stimulation Experiment, left cingulum white matter stimulation, electrodes 16, 22 (FIG. 1), 130 Hz, 300 us pulse width, 1 sec stimulation and sham duration, 10 sec inter-stimulus interval for electrophysiology recording.

| Trial | Current (mA) | Patient Report and Researcher Observations |
|---|---|---|
| 1 | 3.5 mA | Patient immediately smiles, only lasts for a couple seconds |
| 2 | 3.5 mA | Patient immediately smiles, only lasts for couple seconds |
| 3 | 3.5 mA | Patient immediately smiles, only lasts for a couple seconds |
| 4 | Sham | No reported reaction, no change in facial expression |
| 5 | Sham | No reported reaction, no change in facial expression |
| 6 | 3.5 mA | Patient immediately smiles, only lasts for a couple seconds |
| 7 | 3.5 mA | Patient immediately smiles, only lasts for a couple seconds |
| 8 | Sham | No reported reaction, no change in facial expression |
| 9 | 3.5 mA | Patient immediately smiles, only lasts for a couple seconds |
| 10 | Sham | No reported reaction, no change in facial expression |
| 11 | 3.5 mA | Patient immediately smiles, only lasts for a couple seconds |
| 12 | 3.5 mA | Patient immediately smiles, only slightly, lasts for a couple of seconds |
| 13 | 3.5 mA | Patient immediately smiles, only for a couple seconds |
| 14 | Sham | No reported reaction, no change in facial expression |
| 15 | 3.5 mA | Patient immediately smiles, only slightly, lasts for a couple seconds |

TABLE 2-continued

Trial-by-trial patient self-report during cingulate gray and white matter stimulation and sham.

| | | |
|---|---|---|
| 16 | 3.5 mA | Patient immediately smiles, only lasts for a couple seconds |
| 17 | Sham | No reported reaction, no change in facial expression |
| 18 | 3.5 mA | Patient immediately smiles, only slightly, lasts for a couple of seconds |
| 19 | 3.5 mA | Patient immediately smiles, only slightly, lasts for a couple of seconds |
| 20 | Sham | No reported reaction, no change in facial expression |
| 21 | 3.5 mA | Patient immediately smiles, only slightly, lasts for a couple of seconds |
| 22 | 3.5 mA | Patient immediately smiles, only lasts for a couple of seconds |
| 23 | Sham | No reported reaction, no change in facial expression |
| 24 | 3.5 mA | Patient immediately smiles, only lasts for a couple of seconds |
| 25 | Sham | No reported reaction, no change in facial expression |
| 26 | 3.5 mA | Patient immediately smiles, only slightly, lasts for a couple of seconds |
| 27 | 3.5 mA | Patient immediately smiles, only slightly, lasts for a couple of seconds |
| 28 | 3.5 mA | Patient immediately smiles, only lasts for a couple of seconds |
| 29 | 3.5 mA | Patient immediately smiles, only lasts for a couple seconds |
| 30 | Sham | No reported reaction, no change in facial expression |

Researchers ask patient to have normal conversation, without trying to hold back laughter. Stimulation is delivered continuously to the left cingulum white matter, electrodes 16, 22 (FIG. 1), 130 Hz, 300 us pulse width, 2.0 mA.

| Researcher Prompt | Time ON | Patient Response |
|---|---|---|
| "What are you feeling?" | 0:05 | "I can't stop laughing, like I don't know what to say" |
| "Does it feel like someone is tickling you?" | 0:55 | "No, it just feels like I'm laughing and I'm happy and that's what it feels like" |
| "Does it feel like its wearing off?" | 1:17 | "Yeah, I think it wears off a little more over time, and then I start to feel it in my brain" |
| "What does that mean?" | | "I feel more like a weird, high-ish kinda feeling" |
| "Weird-good? Weird-bad? Or just weird-weird?" | 1:36 | "It's weird-weird. I probably couldn't handle it for a long time, because this is kinda how it feels when I have a seizure" |
| "Is it the sense that you're not in control?" | 1:55 | "Yes, exactly. Like I'm not in control" |
| "But not like the exact feeling when you have a seizure?" Just like the sense that you are out of control of your body?" | | "Right" |
| "Would you describe it as euphoria?" | 2:33 | "Yeah, kinda" |
| "Does this feel like sitting and watching a funny movie or being at a comedy club, or does this feel like something else?" | 2:47 | This is something else. It started out feeling like watching a funny movie, and then it turned into a weird feeling" |
| "Do you feel like your threshold to laugh is lower?" | 4:31 | "It's lower, but it's still kinda there" " . . . its more smile now" |
| "And how about that feeling in your face?" | 5:17 | "I still feel like this this side (right corner of mouth) is a little tight and like I don't have control over it, but other than that I can talk normally. I feel like I could function (smiles and laughs)" |
| "Do you think you frown right now?" "Can you try to furrow your brow?" | 5:37 | Patient attempts to frown, but is unsuccessful because she can't turn mouth into a frown. Patient continues to smile and laugh |
| | | Patient attempts to furrow her brow and is able to do it for a very short period of time before she begins to laugh and smile again |
| "Can you think of something sad?" "Can you think of something disgusting?" | 6:11 | "I'm trying to think of my dog dying but it's not working" (laughs and smiles) "Yeah I can think of memories, but they're not coming up as sad memories" |
| Asked to describe a sad memory, and patient begins to talk about her grandfather's funeral | 7:44 | " . . . I almost feel like, right now, my threshold to cry is . . . [really low]" "Yeah. Like I feel like I could burst into tears right now. I don't know why" |
| " . . . can you think of a time that was really disgusting, where you saw something really gross?" "Do you feel sick to your stomach now like you did when you were watching it?" | 9:03 | "I was watching Grey's Anatomy last night, and they were in the burn victim's unit, and for some reason that made me really, really sick. Like it makes me want to vomit. And I remember that as a disgusting memory, but not in a mean way just in a way that would make me kinda sick . . . (inaudible)" "No, actually I don't at all" "I don't feel sick. I just feel this constant happiness" |
| "Does it come in waves?" | 10:25 | "Yes it comes in waves" |
| "How about a memory from longer ago? Like a memory from middle school or something, a happy memory from then?" | 11:38 | "One time I won the science fair. That was really, really, happy" [Patient smiles and laughs] |
| "How about your smile? Can you frown?" | 12:19 | "That does feel a little silly, but I can definitely feel it going away. I feel more in control of over my voice and my emotions" |
| "Do you still feel that happy feeling?" | 13:38 | "I feel happy, but like a normal happy" |
| "How about level of anxiety vs relaxed vs happy?" | 13:47 | "I'm really relaxed. I'm not anxious or anything" |

Legend: Patient self-report was aggregated by an independent rater who reviewed the videos of all patient testing, transcribed all responses, synthesized summary tables and summary statements.

TABLE 3

Documentation of behavioral responses to cingulum bundle stimulation by patient, side, and orientation of electrode array.

| Patient | Mirth | Anxiolysis (Happiness/Relaxation) | Analgesia | Side | Orientation vs. bundle |
|---|---|---|---|---|---|
| 1 | + | + | n/a | left | Parallel |
| 2 | + | + | − | left | Parallel |
| 3 | − | − | n/a | left | Orthogonal |
| 4 | − | − | n/a | left | Orthogonal |
| 5 | − | + | + | right | Parallel |
| 6 | + | + | n/a | right | Parallel |
| 7 | − | + | + | right | Parallel |
| 8 | − | − | + | left | Parallel |
| 9 | − | − | + | left | Parallel |
| 10 | + | + | + | right | Parallel |
| 11 | − | − | n/a | right | Orthogonal |

TABLE 3-continued

Documentation of behavioral responses to cingulum bundle stimulation by patient, side, and orientation of electrode array.

| Patient | Mirth | Anxiolysis (Happiness/ Relaxation) | Analgesia | Side | Orientation vs. bundle |
|---------|-------|-----------------------------------|-----------|-------|-------------------------|
| 12 | − | + | + | right | Parallel |
| 13 | − | − | − | left | Parallel |
| 14 | − | − | − | left | Parallel |
| 15 | − | − | + | right | Parallel |
| 16 | − | + | + | left | Parallel |
| 17 | − | − | − | left | Parallel |
| 18 | − | + | + | left | Parallel |

What is claimed is:

1. A method of stimulating a patient's brain comprising: placing or identifying at least two electrodes, very near to, or in, a portion of an anterior cingulum bundle, and substantially parallel to said portion of said bundle; delivering an electrical stimulation to the electrodes; wherein an electrical field generated in a patient's brain by said stimulation induces substantial activation of white matter; wherein such electrical field induces no activation of fibers of the corpus callosum; wherein such electrical stimulation induces an emotional change in a patient comprising one or more of the following: anxiolysis, mirth, analgesia, improved affective tone, enhanced cognitive focus, increased well-being, engagement, or optimism.

2. The method according to claim 1 wherein at least one electrode is an anode and at least one electrode is a cathode; and, wherein the electrodes are placed within the dorsal portion of the anterior cingulum bundle.

3. The method according to claim 1 wherein the patient is undergoing an awake surgery.

4. The method according to claim 1 wherein the patient is preparing to undergo an awake surgery, or has recently undergone an awake surgery.

5. The method according to claim 1, wherein the patient has undergone a surgery related to the patient's spine and the electrical stimulation is administered to induce said emotional change comprising analgesia; wherein such analgesia is sufficient to reduce administration of some portion of narcotics or to reduce administration of some portion of other pharmaceutical drugs that would have otherwise been administered to treat the patient's pain caused by the surgery.

6. A method of stimulating a patient's brain comprising: placing or identifying at least two electrodes very near to, or in, a portion of an anterior cingulum bundle; delivering an electrical stimulation to the electrodes; wherein the patient has been diagnosed with post-traumatic stress disorder and the electrical stimulation is administered to induce said emotional change comprising anxiolysis to facilitate improved cognitive behavioral therapy or improved psychological or psychiatric intervention(s).

7. The method of claim 2 wherein the patient has been diagnosed with epilepsy and is undergoing an awake craniotomy related to said diagnosis.

8. The method of claim 2 wherein the patient has been diagnosed with a structural brain abnormality, including but not limited to a tumor, or a cavernous malformation and is undergoing an awake craniotomy related to such diagnosis.

9. The method according to claim 6 wherein an electrical field generated in a patient's brain by said stimulation induces no direct activation of fibers of the corpus callosum.

10. The method according to claim 2 wherein at least two electrodes are placed in the dorsal portion of the anterior cingulum bundle in a patient's right hemisphere, and at least two electrodes are placed in the dorsal portion of the anterior cingulum bundle in a patient's left hemisphere.

11. The method of claim 2 wherein the electrodes are spaced between about 0.5 mm and about 76 mm apart.

12. The method of claim 11 wherein the electrodes are spaced between about 5 mm and about 8 mm apart.

13. The method according to claim 2 wherein at least one configuration procedure comprising patient self-report, physiological biomarker, and cognitive biomarker is utilized to determine at least one parameter of said electrical stimulation to achieve at least one emotional change in the patient.

14. The method according to claim 13 wherein the at least one parameter of said electrical stimulation comprises one or more of frequency, current or voltage, or pulse width.

15. The method according to claim 1 wherein said electrical stimulation has parameters comprising over 1.0 mA, between about 50 Hz to about 200 Hz, and having a pulse width of about 90 microseconds to about 450 microseconds.

16. The method according to claim 15 wherein parameters of said electrical stimulation comprise between about 1.0 mA and about 3.5 mA, between about 100 Hz to about 150 Hz, and having a pulse width of about 100 microseconds to about 200 microseconds.

17. The method according to claim 16 wherein parameters of said electrical stimulation comprise between about 2.0 mA and about 3.0 mA, about 90 microseconds pulse width; and about 130 Hz.

18. An apparatus configured to stimulate a patient's brain comprising: at least two electrodes configured to a dorsal portion of an anterior cingulum bundle; at least one power source configured to deliver electrical stimulation to the electrodes; wherein an electrical field generated in a patient's brain by said stimulation induces substantial activation of white matter; wherein such electrical field induces no activation of fibers of the corpus callosum; wherein said stimulation is configured to induce an emotional change in a patient comprising one or more of the following: anxiolysis, mirth, analgesia, improved affective tone, enhanced cognitive focus, increased well-being, engagement, optimism, or any combination thereof; wherein at least one electrode is an anode and at least one electrode is a cathode.

* * * * *